United States Patent
Inada et al.

(10) Patent No.: US 12,411,120 B2
(45) Date of Patent: Sep. 9, 2025

(54) FOOD ANIMAL FRESHNESS/DEGREE OF MATURATION EVALUATING DEVICE, AND FRESHNESS/DEGREE OF MATURATION EVALUATING METHOD

(71) Applicant: NATIONAL UNIVERSITY CORPORATION HOKKAIDO UNIVERSITY, Sapporo (JP)

(72) Inventors: Takaaki Inada, Tsukuba (JP); Hiroshi Nagaishi, Sapporo (JP); Naoto Tsubouchi, Sapporo (JP); Yuji Shinohara, Sapporo (JP)

(73) Assignee: NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 340 days.

(21) Appl. No.: 17/909,459

(22) PCT Filed: Mar. 5, 2021

(86) PCT No.: PCT/JP2021/008597
§ 371 (c)(1),
(2) Date: Sep. 6, 2022

(87) PCT Pub. No.: WO2021/177433
PCT Pub. Date: Sep. 10, 2021

(65) Prior Publication Data
US 2023/0128797 A1  Apr. 27, 2023

(30) Foreign Application Priority Data
Mar. 5, 2020  (JP) ................................ 2020-037546

(51) Int. Cl.
| | | |
|---|---|---|
| G01N 33/12 | (2006.01) | |
| A22B 5/00 | (2006.01) | |
| A22C 29/00 | (2006.01) | |
| A23B 4/06 | (2006.01) | |
| A23B 4/00 | (2006.01) | |
| G06Q 10/0639 | (2023.01) | |

(52) U.S. Cl.
CPC .......... *G01N 33/12* (2013.01); *A22B 5/0064* (2013.01); *A22C 29/005* (2013.01); *A23B 4/06* (2013.01); *A23B 4/00* (2013.01); *G06Q 10/06395* (2013.01)

(58) Field of Classification Search
USPC ......................................................... 702/23
See application file for complete search history.

(56) References Cited

U.S. PATENT DOCUMENTS 5,288,613 A * 2/1994 Luong ................... C12Q 1/005
435/817
2005/0272157 A1  12/2005 Liberman
(Continued)

FOREIGN PATENT DOCUMENTS

| CN | 101358958 A | 2/2009 |
|---|---|---|
| CN | 101539562 A | 9/2009 |

(Continued)

OTHER PUBLICATIONS

Howgate, "Kinetics of Degradation of Adenosine Triphosphate in Chill-Stored Rainbow Trout (*Oncorhynchus mykiss*)," International Journal of Food Science and Technology, 2005, vol. 40, pp. 579-588.

(Continued)

*Primary Examiner* — Paul D Lee
(74) *Attorney, Agent, or Firm* — Oliff PLC

(57) ABSTRACT

A freshness/degree of maturation evaluating device for evaluating freshness and/or degree of maturation of food animal, freshness/degree of maturation evaluating device provided with: temperature parameter calculation unit that calculates temperature parameter regarding storage time and temperature in arbitrary area inside food animal, parameter based on temperature in arbitrary area inside food animal, determined by storage time and unsteady heat conduction equation; rate constant parameter calculation unit that cal- (Continued)

culates rate constant parameter regarding sequential decomposition reactions of various ATP-associated compounds contained infood animal, parameter being set based on rate constants in food animal determined by using relation based on storage time of food animal and measured values of ATP-associated compound concentrations; ATP-associated compound concentration calculation unit that calculates ATP-associated compound concentrations by sequential decomposition reaction calculation model using temperature parameter and rate constant parameter; and freshness/degree of maturation evaluation unit that computes K value and/or FI value from ATP-associated compound concentrations.

19 Claims, 28 Drawing Sheets

(56) References Cited

U.S. PATENT DOCUMENTS

| | | | | |
|---|---|---|---|---|
| 2014/0300891 A1* | 10/2014 | Alfano | ............... | G01N 33/12 356/51 |
| 2016/0092723 A1* | 3/2016 | Kato | ............... | G01N 33/12 382/110 |
| 2016/0123948 A1* | 5/2016 | Bar-Or | ............... | G01N 33/04 436/86 |
| 2017/0190804 A1* | 7/2017 | Michihata | ............... | B32B 27/18 |
| 2021/0140886 A1* | 5/2021 | Taira | ............... | G01N 21/76 |
| 2021/0140887 A1* | 5/2021 | Akiyama | ............... | G01N 33/533 |

FOREIGN PATENT DOCUMENTS

| | | |
|---|---|---|
| CN | 104792950 A | 7/2015 |
| CN | 105116117 A | 12/2015 |
| JP | H06-022684 A | 2/1994 |
| JP | 2857607 B2 | 2/1999 |
| JP | 2008-500810 A | 1/2008 |
| JP | 2009-079966 A | 4/2009 |
| JP | 4291381 B2 | 7/2009 |
| JP | 2013-213810 A | 10/2013 |
| JP | 2018-100935 A | 6/2018 |
| JP | 2020-086841 A | 6/2020 |

OTHER PUBLICATIONS

Feb. 29, 2024 Extended Search Report issued in European Patent Application No. 21764553.0.
May 11, 2021 International Search Report issued in International Patent Application No. PCT/JP2021/008597.
Sep. 6, 2022 International Preliminary Report on Patentability issued in International Patent Application No. PCT/JP2021/008597.
Naomi Ishiwatari; "Prediction of quality changes in meat cooking based on heat transfer analysis"; Master's thesis of Graduate School of Tokyo University of Marine Science and Technology; Mar. 2011; <URL: http://id.nii.ac.ip/1342/00000931/>.
D. Brynn Hibbert et al.; "Mechanism of the hydrolysis of adenosin 5'-Triphosphate: A regression analysis of kinetic data"; Journal of Chemometrics; 1989; vol. 3; pp. 569-577.
Tomoaki Sugawara et al.; "Fluorescence Spectroscopy in Analysis of Raw Scallop Adductor Muscle"; Report of the Hokkaido Industrial Technology Center; 2010; No. 11, 21; pp. 21-24.
Tomoaki Sugawara et al.; "A study of evaluation of freshness by fluorescence spectroscopy in analysis of raw squid mantle muscle"; Report of the Hokkaido Industrial Technology Center; 2012; No. 12, 50; pp. 50-52.
Yoshihiro Yokoyama et al.; "ATP metabolism in muscle after death of fish/shellfish and related items"; Comparative Physiology and Biochemistry; 1998; vol. 15; No. 3; pp. 193-200.
"Investigative research report on quality/freshness indicators to serve as international standards in fisheries"; Kagoshima University Faculty of Fisheries; Nippon Kaiji Kentei Kyokai; Mar. 31, 2014; No. 8; pp. 1-33.
Yukio Yano et al.; "Quality control on intermediate temperature conditioning of beef by measuring cadaverine and hypoxanthine"; Anim. Sci. Technol. (Jpn.); 1992; vol. 63; No. 1; pp. 72-81.
Kunio Numata et al.; "Studies on the indices for estimating freshness of chicken muscles"; Bulletin of the Tokyo-to Agricultural Experiment Station; 1984; No. 17; pp. 20-31.
Atsushi Horiuchi; "Responding to consumer needs in pork production"; All About Swine; 2003; vol. 22; No. 23; pp. 31-41.
Yoshinobu Hiraoka; "Property of wild boar meat"; Bulletin of Aichi Institute of Industrial Technology; 2012; vol. 5; No. 50; pp. 1-4.
Kuniko Sugiyama; "Heated cooking and thermal properties"; Journal of Cookery Science of Japan; 2013; vol. 46; No. 4; pp. 299-303.
Sep. 21, 2024 Office Action issued in Chinese Patent Application No. 202180019153.9.
Ding, W., "Evaluation of Meat Freshness Detection Indicators", Department of Food, Nanjing Agricultural University—210095. 1994, pp. 23-26.
Mar. 28, 2025 Office Action issued in Chinese Patent Application No. 202180019153.9.
Vlas, Carlos, et al. A Model for the Biochemical Degradation of Inosine Monoposphate in Hake (Merluccius Merluccius). Journal of Food Engineering. May 2017.

* cited by examiner

FIG. 31

FOOD ANIMAL FRESHNESS/DEGREE OF MATURATION EVALUATING DEVICE, AND FRESHNESS/DEGREE OF MATURATION EVALUATING METHOD

TECHNICAL FIELD

The present invention relates to a freshness/degree of maturation evaluating device and a freshness/degree of maturation evaluating method that can make highly reliable evaluations regarding the freshness and/or degree of maturation of food animals.

BACKGROUND

In food animals (including aquatic animals, livestock animals, and meat lumps and meat pieces that are portions thereof), the metabolic mechanism known as the ATP (adenosine triphosphate) cycle works while the food animals are alive, thus keeping decay from progressing. However, after death, the cycle no longer works, and ATP decomposes to ADP (adenosine diphosphate), and further decomposes to AMP (adenosine monophosphate), IMP (inosinic acid), AdR (adenosine), HxR (inosine) and Hx (hypoxanthine). Furthermore, although an increase in the amount of IMP improves flavor by creating umami, the amount of IMP generated in aquatic animals is less than that in livestock animals, and at the same time that IMP is being generated, decay rapidly progresses. For this reason, normally, when consumers purchase aquatic animals, they particularly use the "freshness", as observed in the outer appearance, as an indicator thereof.

Meanwhile, in the case of livestock animals, a greater amount of the umami component IMP is generated than in aquatic animals. Furthermore, the progress in decay can be suppressed by taking the preservation conditions into consideration.

Additionally, in Japan, there is a custom in which livestock animals are intentionally left for a certain period of time after being slaughtered. During this period, the meat matures and the IMP amount increases, and this meat is provided to consumers. However, there are differences in the maturation periods due to differences in the types of livestock animals and the preservation conditions. Thus, it is difficult to determine the maturation stage that is optimal for eating by observing the outer appearance alone, and this assessment is difficult even for experienced meat workers. Therefore, taking safety into consideration, the "freshness" as observed in the outer appearance is also currently used as an indicator when most consumers purchase livestock animals.

To explain further regarding aquatic animals, decreases in the freshness of aquatic animals between being caught and being provided to consumers must be suppressed as much as possible. For this reason, the freshness of aquatic animals is maintained by covering aquatic animals that have been caught with ice or the like. Meanwhile, it is important to know, numerically, how much the freshness of an aquatic animal has been maintained during the distribution process. Conventionally, the K value has been used as an indicator for evaluating the freshness of aquatic animals. Additionally, the FI value (see Patent Document 1), which can be used to evaluate the freshness immediately after catch, has recently been proposed. The K value represents, as a percentage (mol %), the sum of the material amount (so-called molar amount) of HxR and the material amount of Hx relative to the total material amount of ATP and reaction products thereof, $$K \text{ value} = (\text{HxR amount} + \text{Hx amount})/(\text{ATP amount} + \text{ADP amount} + \text{AMP amount} + \text{IMP amount} + \text{AdR amount} + \text{HxR amount} + \text{Hx amount}) \times 100$$

The K value has been experimentally determined to indicate the "freshness" of an aquatic animal by the magnitude of said value, and a lower K value is considered to indicate higher freshness. For example, in the case of aquatic animals, a K value of 20 or lower is considered to indicate freshness and suitability for raw consumption, as in sashimi or sushi. When the upper limit of 20 is exceeded, the freshness is lost and the aquatic animal becomes inappropriate for raw consumption (see Patent Document 2).

Meanwhile, the FI value is computed on the basis of the following expression (see Patent Document 1).

$$\text{FI value} = \{\text{ATP amount} - (\text{HxR amount} + \text{Hx amount})\}/(\text{ATP amount} + \text{ADP amount} + \text{AMP amount} + \text{IMP amount} + \text{AdR amount} + \text{HxR amount} + \text{Hx amount})$$

The H value can be used to evaluate a wider range of aquatic animal species, for example, mollusks in which the decomposition pathway involves AdR, than the K value can. In aquatic animal species in which AdR is generated, the denominator is undervalued in the expression for computing the K value. Thus, there is a possibility that the K value will be overvalued relative to the actual freshness state. Additionally, compared to the K value, the numerical variations in the freshness evaluation immediately after death are large and thus easy to visualize. Furthermore, as the freshness declines, the numerical value also decreases, thus matching the image of the freshness change among general consumers and making it easy to use as a freshness evaluation display method.

The higher the FI value is, the fresher that aquatic animal is. Thus, the magnitude of that value can be used to determine the "freshness" of an aquatic animal. For example, in the case of aquatic animals, if the FI value is 0 or higher, then a state that is so extremely fresh that it cannot be evaluated by a K value can be evaluated numerically. Values down to approximately −0.2 are determined as indicating suitability for raw consumption, as in sashimi or sushi. Additionally, as the lower limit value becomes smaller than −0.2, the freshness is lost, and a value of −0.6 or lower indicates non-suitability for raw consumption.

Although the ATP in aquatic animals is consumed by biological activity and thus decomposes to ADP, respiration regenerates the ATP. However, when respiration stops after death, the supply of oxygen is cut off and ATP regeneration stops. ATP then begins to decompose by the main pathways indicated below.

Fish: ATP→ADP→AMP→IMP→HxR→Hx

Mollusks: ATP→ADP→AMP→AdR→HxR→Hx

Crustaceans: ATP→ADP→AMP→(IMP and/or AdR)→HxR→Hx

Thus, the state of decline in the freshness of an aquatic animal can be known from a comparison between the amount of ATP and the amount of ATP-derived decomposition products, thus allowing the level of freshness to be known.

Furthermore, examples of the aquatic animals in the present invention include seafood and aquatic mammals. Examples of seafood include fish, shellfish, mollusks (other than shellfish), protochordates, echinoderms, crustaceans, and coelenterates. Examples of mollusks include squids and octopuses. Examples of protochordates include sea squirts.

Examples of echinoderms include sea cucumbers and sea urchins. Examples of crustaceans include crabs and shrimp. Examples of coelenterates include jellyfish. Examples of aquatic mammals include whales and dolphins.

Additionally, as mentioned above, in evaluation methods based on the K value, the K value is defined as the total percentage of HxR and Hx included in ATP-associated compounds generated from ATP after death, and the freshness is evaluated by the magnitude thereof. After sampling a certain portion of an aquatic animal after death, the pretreated sample is subjected to component analysis by a liquid chromatograph, and a numerical value is obtained by defining the sum of the amounts of components of ATP-associated compounds in the sample to be the denominator, and the total amount of HxR and Hx to be the numerator.

This technology has the problem that the pretreatment requires expert knowledge and skill, and measurements cannot be made without at least a certain level of skill and experience. Additionally, in order to obtain an evaluation by K value, several hours are required to pretreat the sample and to perform component analysis after the pretreatment. Thus, there is the drawback that freshness evaluations by K value are difficult to perform in fields requiring the freshness to be known quickly, for example, at distribution sites.

Meanwhile, there has been interest in methods for evaluating freshness from optical properties. For example, for scallop adductor muscles and Japanese flying squid, there are freshness evaluation methods (fluorescence spectroscopy methods) that use the fluorescence intensity of amino acids and proteins as indicators (see Non-Patent Documents 1 and 2). In general, fluorescence spectroscopy allows quick, non-destructive high-sensitivity analysis. Thus, autofluorescence measurement can be considered to be usable for evaluating freshness without pretreatment. However, it is difficult to use at distribution sites.

The reason for this is that, due to the high sensitivity, randomness in the measurement optical system caused by factors such as the shape of a sample can affect fluorescence. In order to reduce the error, the measurement system must be put in identical states. However, in order to realize this, the irradiation angle of the excitation light, the fluorescent light generation range, and the fluorescent light detection area must be kept uniform. For example, it is difficult to precisely immobilize targets that are curved or that have irregularities. Thus, there are many problems in use at distribution sites.

Aside from the above, a method for assessing the freshness of meat has been disclosed, wherein the method involves using a micropipette to spot-drop a fixed amount of a supernatant obtained by placing, at rest, a piece of meat that has been homogenized by using an aqueous deproteinizer solution, onto an origin point on electrophoretic filter paper that has been set on an electrophoresis frame and wetted with an electrophoresis buffer solution, and immediately performing electrophoresis, then radiating ultraviolet rays thereon and comparatively observing the sizes and concentrations of spots of nucleic acid-associated compounds that rise and performing relative comparisons of the origin point and movement (see Patent Document 3).

Additionally, a method for measuring the freshness of an aquatic animal from a concentration ratio between ATP-associated compounds contained in fish meat, specifically, a method of quickly computing a K value by an FIA method (flow analysis method) to assess the freshness of an aquatic animal in a short time has been disclosed (see Patent Document 4). Furthermore, Patent Document 5 discloses a method that involves slicing a small amount of a sample from an aquatic animal, adding an effective amount of a coloring reagent containing at least one cell-permeable dye and a cell-impermeable dye to the sample, incubating this sample for a certain period of time, and determining the freshness based on fluorescent light emitted from the sample. Additionally, Patent Document 6 discloses a method for evaluating the freshness of an aquatic animal by non-destructively evaluating, without pre-treatment, the freshness of raw cells of the aquatic animal by measuring the intensity of fluorescent light from nicotinamide adenine dinucleotide acid, which is a type of coenzyme contained in aquatic animals. However, all of these methods require high-precision, high-sensitivity optical measurement devices to be installed, and require aquatic animals to be directly measured one at a time. Thus, they are difficult to use as methods for evaluating freshness or degree of maturation at distribution sites.

Meanwhile, a low-temperature preservation apparatus has been disclosed, wherein the low-temperature preservation apparatus detects the temperature of food products without contact and records the temperature over time, and displays K values and metmyoglobin formation rates indicating the freshness of food products in accordance with the passage of preservation time, computed by using frequency factors and activation energy values obtained as a result of experiments (see Patent Document 2). However, this is difficult to use as a method for evaluating freshness or degree of maturation at distribution sites.

The reason for this is because, in the decomposition reactions of ATP-associated compounds generated from ATP after the death of aquatic animals, the fact that the decomposition rates in various types of decomposition processes of ATP-associated compounds differ depending on the type of aquatic animal is clear from the concentration changes in the respective components of ATP-associated compounds over time. For this reason, this method has the drawback that it is difficult to precisely determine the K values of various aquatic animals with a single computational expression using only the values of frequency factors and activation energies obtained as a result of experiments. Additionally, the present invention also includes methods for using the concentrations of certain specific ATP-associated compounds to evaluate the degree of maturation, and it is impossible to use the calculation method in Patent Document 2 to determine concentration changes of various types of ATP-associated compounds with respect to storage time.

To explain further regarding livestock animals, as with fish meat, evaluation methods for accurately evaluating the freshness of livestock meat have been studied. For example, although measurements of pH, volatile basic nitrogen (VBN), viable cell count, and the like have been used as indicators for storage control and the like, these cannot be considered to be methods that are sufficient for precisely determining the freshness before decay.

Thus, evaluations of beef (Non-Patent Document 5), chicken (Non-Patent Document 6), pork (Non-Patent Document 7), boar meat (Non-Patent Document 8), etc. have come to be performed by using evaluation methods that are the same as the K value computation method in fish meat, which was already being used to evaluate freshness.

The livestock animals in the present invention are not particularly limited, and examples include fowl, domesticated stock, game (wild birds and animals), etc. Examples of fowl include chickens, ostriches, guinea fowl, turkeys, pigeons, etc.

Examples of domesticated stock include cattle, water buffaloes, horses, goats, sheep, pigs, etc. Examples of game include mallards, ducks, partridges, pheasants, grouse, woodcocks, hares, deer, boars, bears, raccoons, frogs, etc.

However, as with the freshness evaluations of aquatic animals, there is no method for evaluating K values or FI values in real-time at distribution sites in the case of livestock animals as well. Among currently proposed methods, a method of directly measuring the impedance of meat (Patent Document 7) might be contemplated as a practical method to be used at distribution sites. However, this method requires preliminary work to acquire measurement data at a variety of temperatures regarding the K values or H values of various types of meat in advance and to associate the values with impedance ratios. Furthermore, temporal change information regarding transportation times and storage temperatures is practically impossible to associate with impedance ratios.

CITATION LIST

Patent Literature

Patent Document 1: JP 2018-100935 A
Patent Document 2: JP H6-22684 A
Patent Document 3: JP 4291381 B
Patent Document 4: JP 2857607 B
Patent Document 5: JP 2008-500810 A
Patent Document 6: JP 2013-213810 A
Patent Document 7: JP 2009-79966 A Non-Patent Literature Non-Patent Document 1: Tomoaki SUGAWARA, Yasutomo NOMURA, Sense KATO, Takeya YOSHIOKA, Yasunori KINOSHITA and Isao ODA, "Fluorescence Spectroscopy in Analysis of Raw Scallop Adductor Muscle", Report of the Hokkaido Industrial Technology Center, No. 11, 21 (2010)

Non-Patent Document 2: Tomoaki SUGAWARA, Yasutomo NOMURA, Sanae KATO, Takeya YOSHIOKA, Yasunori KINOSHITA and Isao ODA, "A Study of Evaluation of Freshness by Fluorescence Spectroscopy in Analysis of Raw Squid Mantle Muscle", Report of the Hokkaido Industrial Technology Center, No. 12, 50 (2012)

Non-Patent Document 3: Yoshihiro YOKOYAMA and Morihiko SAKAGUCHI, "ATP metabolism in muscle after death of fish/shellfish and related items", Hikaku seiri seikagaku (Comparative Physiology and Biochemistry), Vol. 15, No. 3, 193 (1998)

Non-Patent Document 4: NIPPON KAIJI KENTEI KYOKAI (FOOD HYGIENE ANALYSIS CENTER), KAGOSHIMA UNIVERSITY FACULTY OF FISHERIES, "Suisanbutsu-to no kokusai-hyojun to naru hinshitsu/sendoshihyo ni kansuru chosa-kenkyu-hokokusho" [Investigative research report on quality/freshness indicators to serve as international standards in fisheries, etc.], 8, Mar. 31, 2014

Non-Patent Document 5: Yukio YANO, Fumie MURAYAMA, Nobuko KATAHO, Ming TACHIBANA and Toyoo NAKAMURA, "Quality Control on Intermediate Temperature Conditioning of Beef by Measuring Cadaverine and Hypoxanthine", Anim. Sci. Technol. (Jpn.), 63(1), 72-81 (1992)

Non-Patent Document 6: Kunio NUMATA and Hiroshi SUZUKI, "Studies on the Indices for Estimating Freshness of Chicken Muscles", Bulletin of the Tokyo-to Agricultural Experiment Station, No. 17, 20-31 (1984)

Non-Patent Document 7: Atsushi HORIUCHI, "Butaniku-seisan ni okeru shohisha niizu e no taio" [Responding to consumer needs in pork production], AH About Swine, 22/23, 31-41 (2003)

Non-Patent Document 8: Yoshinobu HIRAOKA, "Property of Wild Boar Meat", Bulletin of Aichi Institute of Industrial Technology, Vol. 5, No. 50, 1-4 (2012)

Non-Patent Document 9: Kuniko SUGIYAMA, "Kanetsu-chori to netsu-bussei" [Heated cooking and thermal properties], Journal of Cookery Science of Japan, Vol. 46, No. 4, 299-303 (2013)

SUMMARY OF INVENTION

Technical Problem

As mentioned above, the freshness of food animals can still only be measured by methods that involve acquiring concentration information regarding ATP-associated compounds directly from the food animals each time to perform the evaluation by using K values or FI values as an indicator, by methods of evaluation by directly measuring coenzymes contained in the food animals, and by methods of electrical measurement. Thus, there were problems in that the temporal change in freshness cannot be determined by using the freshness of the food animal at the time of catch or slaughter as a reference, the freshness cannot be evaluated in real time at distribution sites, and consumers cannot obtain this information in real time. Therefore, there is a demand to develop a method for evaluating freshness/degree of maturation in real time, at distribution sites, using IMP values, K values, or FI values as indicators, without directly measuring the meat of food animals, by practically performing simulations taking into account transient changes in the killing/cooling processes at the time of catch or slaughter, in which there are large temperature changes in the meat, distribution/storage processes in which the environmental temperature is controlled, and the like, Solution to Problem The present invention was made in order to respond to such needs, and the means for solving the problem addressed thereby is to provide a freshness/degree of maturation evaluating device and a freshness/degree of maturation evaluating method allowing the freshness and/or the degree of maturation during a food animal distribution process to be evaluated by appropriately taking into account transient changes also. Thus, the present invention, described below, was completed. The gist of the present invention, for solving the above-mentioned problem, is indicated below.

(1) The freshness/degree of maturation evaluating device for evaluating a freshness and/or a degree of maturation of a food animal according to the present invention is provided with: a temperature parameter calculation unit that calculates a temperature parameter regarding a storage time and a temperature in an arbitrary area inside the food animal, the parameter being based on the temperature in the arbitrary area inside the food animal, determined by the storage time and an unsteady heat conduction equation; a rate constant parameter calculation unit that calculates a rate constant parameter regarding sequential decomposition reactions of various ATP-associated compounds contained in the food animal, the parameter being set based on rate constants in the food animal determined by using a relation based on the storage time of the food animal and measured values of ATP-associated compound concentrations; an ATP-associated compound concentration calculation unit that calculates the ATP-associated compound concentrations by a sequential decomposition reaction calculation model using the temperature parameter and the rate constant parameter; and a freshness/degree of maturation evaluation unit that computes a K value and/or an FI value from the ATP-associated compound concentrations.

(2) The freshness/degree of maturation evaluating device for evaluating a freshness and/or a degree of maturation of a food animal according to the present invention is provided with: a rate constant parameter calculation unit that calculates a rate constant parameter regarding sequential decomposition reactions of various ATP-associated compounds contained in the food animal, the parameter being set based on rate constants in the food animal determined by using a relation based on a storage time of the food animal and measured values of ATP-associated compound concentrations; an ATP-associated compound concentration calculation unit that calculates the ATP-associated compound concentrations by a sequential decomposition reaction calculation model using a storage temperature of the food animal and the rate constant parameter; and a freshness/degree of maturation evaluation unit that computes a K value and/or an FI value from the ATP-associated compound concentrations.

(3) According to one embodiment of the present invention, in the freshness/degree of maturation evaluating device according to (1) or (2) above, the food animal is an aquatic animal.

(4) According to one embodiment of the present invention, in the freshness/degree of maturation evaluating device according to (3) above, the aquatic animal is one of sweetfish, chub mackerel, Japanese jack mackerel, olive flounder, skipjack tuna, Pacific saury, Japanese amberjack, red seabream, young Japanese amberjack, Spanish mackerel, Japanese pilchard, Japanese flying squid, Toyama shrimp, scallop, and sea urchin.

(5) According to one embodiment of the present invention, in the freshness/degree of maturation evaluating device according to (1) or (2) above, the food animal is a livestock animal.

(6) According to one embodiment of the present invention, in the freshness/degree of maturation evaluating device according to (5) above, the livestock animal is one of a cow, a chicken, a pig, and a boar.

(7) According to one embodiment of the present invention, in the freshness/degree of maturation evaluating device according to any one of (1) to (6) above, at least two and at most ten of the rate constant parameters are used.

(8) According to one embodiment of the present invention, in the freshness/degree of maturation evaluating device according to any one of (1) to (7) above, the freshness/degree of maturation evaluation unit further evaluates the freshness and/or the degree of maturation of the food animal by comparing at least one of the K value, the FI value, or an IMP value with a prescribed threshold value.

(9) According to one embodiment of the present invention, in the freshness/degree of maturation evaluating device according to any one of (1) to (7) above, the freshness/degree of maturation evaluation unit computes an mK value from the ATP-associated compound concentrations, and further evaluates the freshness and/or the degree of maturation of the food animal by comparing the mK value or both the mK value and the IMP value with a prescribed threshold value.

(10) According to one embodiment of the present invention, the freshness/degree of maturation evaluating device according to (8) above further comprises a freshness/degree of maturation assessment unit that assesses the freshness and/or the degree of maturation by comparing an evaluation result by the freshness/degree of maturation evaluation unit with a prescribed threshold value.

(11) According to one embodiment of the present invention, the freshness/degree of maturation evaluating device according to (9) above further comprises a freshness/degree of maturation assessment unit that assesses the freshness and/or the degree of maturation by comparing an evaluation result by the freshness/degree of maturation evaluation unit with a prescribed threshold value.

(12) According to one embodiment of the present invention, in the freshness/degree of maturation evaluating device according to (10) above, the freshness/degree of maturation assessment unit has functions for assessing the freshness and/or the degree of maturation of the food animal by comparing at least one of the K value, the FI value, or the IMP value with a prescribed threshold value, and for displaying optimal recommended cooking information regarding an ingredient in accordance with the assessment result,

(13) According to one embodiment of the present invention, in the freshness/degree of maturation evaluating device according to (11) above, the freshness/degree of maturation assessment unit has functions for assessing the freshness and/or the degree of maturation of the food animal by comparing the m K value or both the mK value and the IMP value with a prescribed threshold value, and for displaying optimal recommended cooking information regarding an ingredient in accordance with the assessment result.

(14) According to one embodiment of the present invention, in the freshness/degree of maturation evaluating device according to any one of (10) to (13) above, the freshness/degree of maturation assessment unit has a system for sequentially displaying, on a map, arbitrary waypoints on a transportation path, and has a function wherein, when a transit location is designated on the map, a temperature change and freshness information at a relevant location on the map, and a freshness or a storage temperature at a designated time, can be visually confirmed.

(15) According to one embodiment of the present invention, in the freshness/degree of maturation evaluating device according to any one of (10) to (14) above, the freshness/degree of maturation assessment unit has functions for computing necessary conditions, such as an optimized storage temperature, a storage time, a transportation method, a transportation path, a catch/slaughter date/time, and a transportation commencement date/time, satisfying ordering conditions, and for automatically inputting initial settings values for transportation conditions satisfying consumer needs.

(16) According to one embodiment of the present invention, in the freshness/degree of maturation evaluating device according to any one of (10) to (15) above, the freshness/degree of maturation assessment unit has functions for displaying cautionary information, in a case in which there has been an outbreak of an infectious disease among distribution-associated people on a distribution path, and if a food animal is determined to be unsafe to eat or if considerable caution is determined to be necessary from the freshness/degree of maturation assessment results and processing information based on fishery-, slaughter-, processing-, market-, and distribution-associated person data, distribution transit location information, and disinfection/sterilization data.

(17) According to one embodiment of the present invention, a refrigerator/freezer is provided with the freshness/degree of maturation evaluating device according to any one of (1) to (16) above.

(18) The freshness/degree of maturation evaluating method for evaluating a freshness and/or a degree of maturation of a food animal according to the present invention includes: a temperature parameter calculation step for calculating a temperature parameter regarding a storage time and a temperature in an arbitrary area inside the food animal, the parameter being based on the temperature in the arbitrary area inside the food animal, determined by the storage time and an unsteady heat conduction equation; a rate constant parameter calculation step for calculating a rate constant parameter regarding sequential decomposition reactions of various ATP-associated compounds contained in the food animal, the parameter being set based on rate constants in the food animal determined by using a relation based on the storage time of the food animal and measured values of ATP-associated compound concentrations; an ATP-associated compound concentration calculation step for calculating the ATP-associated compound concentrations by a sequential decomposition reaction calculation model using the temperature parameter and the rate constant parameter; and a freshness/degree of maturation evaluation step for computing a K value and/or an FI value from the ATP-associated compound concentrations.

(19) The freshness/degree of maturation evaluating method for evaluating a freshness and/or a degree of maturation of a food animal according to the present invention includes: a rate constant parameter calculation step for calculating a rate constant parameter regarding sequential decomposition reactions of various ATP-associated compounds contained in the food animal, the parameter being set based on rate constants in the food animal determined by using a relation based on a storage time of the food animal and measured values of ATP-associated compound concentrations; an ATP-associated compound concentration calculation step for calculating the ATP-associated compound concentrations by a sequential decomposition reaction calculation model using a storage temperature of the food animal and the rate constant parameter; and a freshness/degree of maturation evaluation step for computing a K value and/or an FI value from the ATP-associated compound concentrations.

(20) According to one embodiment of the present invention, in the freshness/degree of maturation evaluating method according to (18) or (19) above, the food animal is an aquatic animal.

(21) According to one embodiment of the present invention, in the freshness/degree of maturation evaluating method according to (20) above, the aquatic animal is one of sweetfish, chub mackerel, Japanese jack mackerel, olive flounder, skipjack tuna, Pacific saury, Japanese amberjack, red seabream, young Japanese amberjack, Spanish mackerel, Japanese pilchard, Japanese flying squid, Toyama shrimp, scallop, and sea urchin.

(22) According to one embodiment of the present invention, in the freshness/degree of maturation evaluating method according to (18) or (19) above, the food animal is a livestock animal.

(23) According to one embodiment of the present invention, in the freshness/degree of maturation evaluating method according to (22) above, the livestock animal is one of a cow, a chicken, a pig, and a boar.

(24) According to one embodiment of the present invention, in the freshness/degree of maturation evaluating method according to any one of (18) to (23) above, at least two and at most ten of the rate constant parameters are used.

(25) According to one embodiment of the present invention, in the freshness/degree of maturation evaluating method according to any one of (18) to (24) above, the freshness/degree of maturation evaluation step further involves evaluating the freshness and/or the degree of maturation of the food animal by comparing at least one of the K value, the H value, or an IMP value with a prescribed threshold value.

(26) According to one embodiment of the present invention, in the freshness/degree of maturation evaluating method according to any one of (18) to (24) above, the freshness/degree of maturation evaluation step involves computing an mK value from the ATP-associated compound concentrations, and further evaluating the freshness and/or the degree of maturation of the food animal by comparing the mK value or both the mK value and the IMP value with a prescribed threshold value.

(27) According to one embodiment of the present invention, the freshness/degree of maturation evaluating method according to (25) above further comprises a freshness/degree of maturation assessment step for assessing the freshness and/or the degree of maturation by comparing an evaluation result from the freshness/degree of maturation evaluation step with a prescribed threshold value,

(28) According to one embodiment of the present invention, the freshness/degree of maturation evaluating method according to (26) above further comprises a freshness/degree of maturation assessment step for assessing the freshness and/or the degree of maturation by comparing an evaluation result from the freshness/degree of maturation evaluation step with a prescribed threshold value.

(29) According to one embodiment of the present invention, in the freshness/degree of maturation evaluating method according to (27) above, the freshness/degree of maturation assessment step includes functions for assessing the freshness and/or the degree of maturation of the food animal by comparing at least one of the K value, the FI value, or the IMP value with a prescribed threshold value, and for displaying optimal recommended cooking information regarding an ingredient in accordance with the assessment result.

(30) According to one embodiment of the present invention, in the freshness/degree of maturation evaluating method according to (28) above, the freshness/degree of maturation assessment step includes functions for assessing the freshness and/or the degree of maturation of the food animal by comparing the mK value or both the mK value and the IMP value with a prescribed threshold value, and for displaying optimal recommended cooking information regarding an ingredient in accordance with the assessment result.

(31) According to one embodiment of the present invention, in the freshness/degree of maturation evaluating method according to any one of (27) to (30) above, the freshness/degree of maturation assessment step has a system for sequentially displaying, on a map, arbitrary waypoints on a transportation path, and includes a function wherein, when a transit location is designated on the map, a temperature change and freshness information at a relevant location on the map, and a freshness or a storage temperature at a designated time, can be visually confirmed.

(32) According to one embodiment of the present invention, in the freshness/degree of maturation evaluating method according to any one of (27) to (31) above, the freshness/degree of maturation assessment step includes functions for computing necessary conditions, such as an optimized storage temperature, a storage time, a transportation method, a transportation path, a catch/slaughter date/time, and a transportation commencement date/time, satisfying ordering conditions, and for automatically inputting initial settings values for transportation conditions satisfying consumer needs.

(33) According to one embodiment of the present invention, in the freshness/degree of maturation evaluating method according to any one of (27) to (32) above, the freshness/degree of maturation assessment step includes functions for displaying cautionary information, in a case in which there has been an outbreak of an infectious disease among distribution-associated people on a distribution path, and if a food animal is determined to be unsafe to eat or if considerable caution is determined to be necessary from the freshness/degree of maturation assessment results and processing information based on fishery-, slaughter-, processing-, market-, and distribution-associated person data, distribution transit location information, and disinfection/sterilization data

(34) According to one embodiment of the present invention, a refrigerator/freezer uses the freshness/degree of maturation evaluating method according to any one of (18) to (33).

In order to allow the temperature parameter to be easily set, the temperature parameter can be set by setting the number of divisions in temperature areas (the sizes of the areas) determined by the above-mentioned unsteady heat conduction equation in accordance with the purpose. That is, the temperature parameter is set by computing storage times and temperatures or temperature changes, in arbitrary areas inside a food animal, by means of an unsteady heat conduction equation, from food animal type and shape information, the temperatures of crushed ice in which the food animal or the meat thereof is immersed during a distribution process, and the storage temperature in the periphery of the food animal. As a result thereof, reaction temperatures can be set with the same level of accuracy as the temperatures in the arbitrary areas inside the actual food animal. Therefore, the simulations by the sequential decomposition reaction constitution formulas for the ATP-associated compounds can be made more accurate.

In the same food animal species, the differences in heat conduction due to differences in the amount of fat on individuals or in shapes, such as the sizes, are small. Thus, only the influence of the temperature at the arbitrary areas inside the food animal need to be considered regarding ATP-associated compound decomposition reactions.

Additionally, the ATP-associated compound decomposition reactions inside food animals are fundamentally enzyme reactions (Non-Patent Document 3). Thus, enzymes and substrates, enzyme-substrate complexes and enzyme-product complexes need to be considered. However, in ATP-associated compound decomposition reactions, the products are immediately released from enzyme-product complexes. Thus, the decomposition reactions from the enzyme and the substrate to the release of the objective products can be approximated by a single decomposition reaction, allowing the reactions to be represented by sequential decomposition reaction constitution formulas comprising ATP→ADP, ADP→AMP, AMP→IMP, IMP→HxR, and HxR→Hx; ATP→ADP, ADP→AMP, AMP→AdR, AdR→HxR, and HxR→Hx; ATP+ADP+AMP→IMP and IMP→HxR+Hx, and the reverse reactions thereof.

Effects of Invention

According to the present invention as described above, the level of quality in the freshness and/or the degree of maturation of a food animal can be assessed by evaluating the freshness and/or the degree of maturation of the food animal during the distribution/storage process, from the time of catch or slaughter, by appropriately taking into account transient changes.

BRIEF DESCRIPTION OF DRAWINGS

FIG. 31 is a diagram illustrating an example of a display of calculation results.

DESCRIPTION OF EMBODIMENTS

Hereinafter, an embodiment of the present invention will be explained in detail. However, the explanations of constituent features provided below relate to representative examples of embodiments of the present invention, and the present invention can be implemented by making modifications, as appropriate, within a range not departing from the spirit of the present invention.

Figure 1:
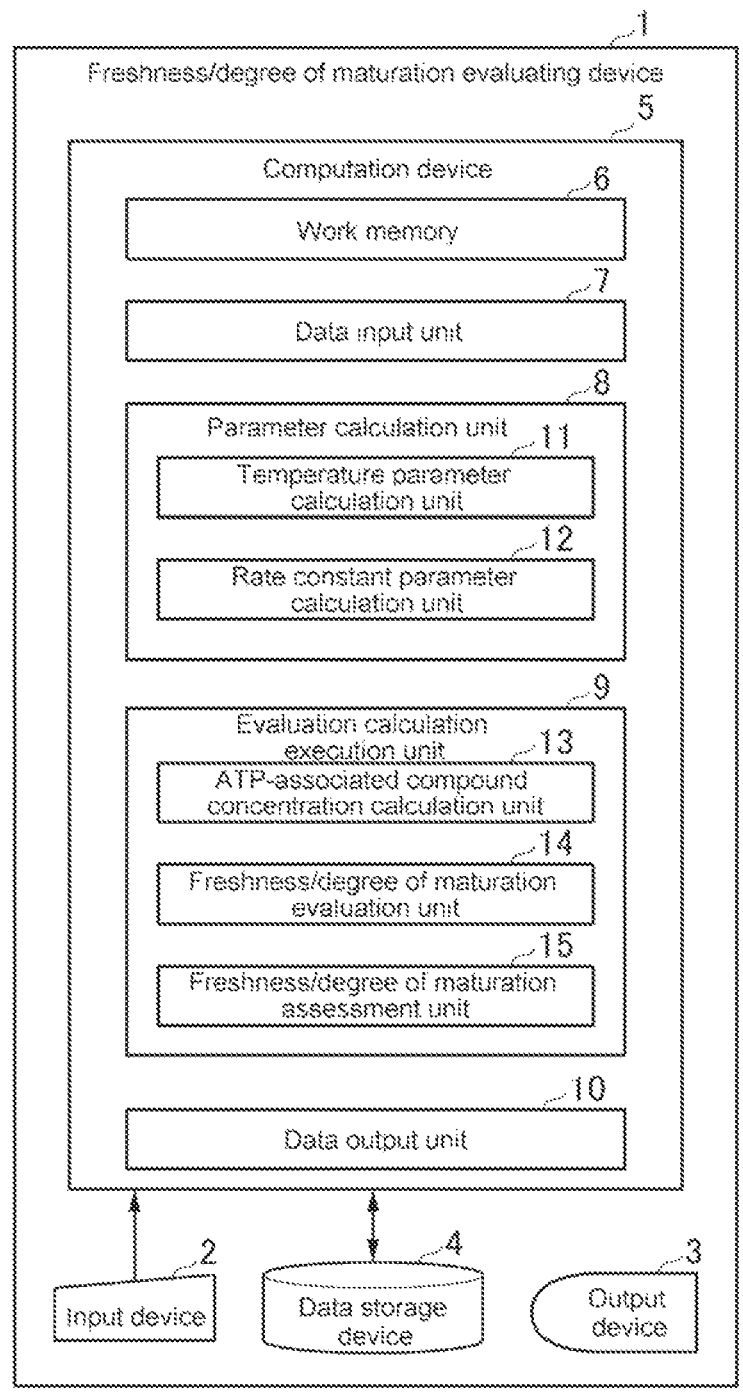
FIG. 1 is a diagram schematically illustrating the structure of a food animal freshness/degree of maturation evaluating device according to one embodiment.

FIG. 1 is a diagram schematically illustrating the structure of a food animal freshness/degree of maturation evaluating device 1 according to one embodiment. The food animal freshness/degree of maturation evaluating device 1 computes the temporal change in the K value and/or the FI value by using simulations to determine the temporal change in the concentrations of various types of components by means of sequential decomposition reaction constitution formulas including ATP→ADP, ADP→AMP, AMP→IMP. IMP→HxR, and HxR→Hx; ATP→ADP, ADP→AMP, AMP→AdR, AdR→HxR, and HxR→Hx; or ATP+ADP+AMP→IMP and IMP→HxR Hx; and the reverse reactions thereof. Furthermore, the freshness/degree of maturation evaluating device 1, based on the temporal change in at least one of the K value, the FI value, or the IMP value, computes the storage time until at least one of the K value, the FI value, or the IMP value becomes a preset value (prescribed threshold value), or computes at least one of the K value, the FI value, or the IMP value at a set storage time (prescribed threshold value). Furthermore, the freshness/degree of maturation evaluating device 1 compares the evaluation results with a preset threshold value (prescribed threshold value) to assess the level of quality in the freshness and/or the degree of maturation in the food animal. In order to do so, the food animal freshness/degree of maturation evaluating device 1 is provided with an input device 2, an output device 3, a data storage device 4, and a computation device 5.

The input device 2 is constituted, for example, by a keyboard and mouse, an RF (radio frequency) tag reading device, or the like, and is used by a user to input data or the like necessary for simulations. The output device 3 is constituted, for example, by a display device, a printer device, or the like, and is used to output simulation results or the like. The data storage device 4 is used to store data, simulation results, or the like necessary for simulations.

The computation device 5 executes various types of processes during simulations, and performs evaluations of the freshness and/or degree of maturation of food animals. For this purpose, the computation device 5 is provided with a work memory 6 that functions to temporarily hold data, processing results, and the like necessary for the processing in the computation device 5, and is also provided with a data input unit 7, a parameter setting unit 8, a calculation execution unit 9, and a data output unit 10 that are respectively configured as computer programs.

The data input unit 7 registers, in the work memory 6, data input by means of the input device 2, data read from the data storage device 4 under instructions provided via the input device 2, or the like. Examples of the data in this case include livestock animal species data, aquatic animal species data, breed data, form data (size data, weight data, etc.), catch/slaughter/cultivation/farming location data (map data, latitude/longitude data, etc.), catch/slaughter time data, fishing-, farming-, meat processing-, transportation-, sale-, wholesale-, market-, and distribution-associated person data (affiliation data (detailed data such as affiliated ships/fish farms/ranches/pig farms/chicken farms, etc.), name data, health status data, infectious disease data (coronavirus disease 2019 (COVID-19, etc.), bacterial food poisoning (*Vibrio parahaemolyticus*; pathogenic *Escherichia coli*, *Salmonella*, *Campylobacter*, *Staphylococcus aureus*, enterohemorrhagic *Escherichia Clostridium perfringens*, etc.), viral food poisoning (norovirus, etc.)), killing/slaughtering method data (severing the neck after stunning, severing the neck without stunning, severing the neck after stunning with gas, beating, icing, bleeding, ike-jime, shinkei-jime, asphyxiation, etc.), storage temperature data (measurement data recording changes in the storage temperature with respect to the storage time), storage commencement time data, starer data, ice data (ice slurry data, crushed ice data, snow-type ice data, temperature data, ice/water ratio data, data regarding the seawater salt concentration at the time of icemaking, etc.), transportation box data (material data, size data, heat transfer characteristics data, etc.), disinfection/sterilization data (processing method data, processing time data, processing date/time data, effects data, etc.), coolant data (type data, usage amount data, manufacturing location data, etc.), measurement data regarding ATP-associated reaction product concentration changes in the same food animal species at two or more different storage temperatures (documented value data, measured value data, etc.), and data regarding constants necessary for solutions to unsteady heat conduction equations for each food animal species (thermal conductivity k, food animal meat density p, specific heat c, generated heat Q, etc.). Some of the aforementioned data may be realized by preparing, in advance, a database classified by the catch time, the catch location, or the like, for each food animal species, and by reading the necessary data by connecting the database to the data storage device 4.

The parameter calculation unit 8 calculates temperature parameters and rate constant parameters. In order to do so, it has a temperature parameter calculation unit 11 for calculating temperature parameters, and a rate constant parameter calculation unit 12 for calculating rate constant parameters. In the present embodiment, the temperature parameters are parameters relating to temperatures necessary for computing ATP-associated reaction compounds used in the sequential decomposition reaction constitution formulas including ATP→ADP, ADP→AMP, AMP→IMP, IMP→HxR, and HxR→Hx; ATP→ADP, ADP→AMP, AMP→AdR, AdR→HxR, and HxR→Hx; or ATP+ADP+ AMP→IMP and IMP→HxR+Hx; and the reverse reactions thereof. The speed constant parameters are parameters necessary for computing the concentrations of ATP-associated reaction compounds by means of the sequential decomposition reaction constitution formulas similarly including ATP→ADP, ADP→AMP, AMP→IMP, IMP→HxR, and HxR→Hx; ATP→ADP, ADP→AMP, AMP→AdR, AdR→HxR, and HxR→Hx; or ATP+ADP+AMP→IMP and IMP→HxR+Hx; and the reverse reactions thereof. Details regarding the calculation of the temperature parameters by the temperature parameter calculation unit 11 in the parameter calculation unit 8 and the calculation of the rate constant parameters by the rate constant parameter calculation unit 12 in the parameter calculation unit 8 will be explained below.

The evaluation calculation execution unit 9 has an ATP-associated compound concentration calculation unit 13, a freshness/degree of maturation evaluation unit 14, and a freshness/degree of maturation assessment unit 15. The ATP-associated compound concentration calculation unit 13 calculates the change in the concentration of ATP-associated compounds by means of simulations. The freshness/degree of maturation evaluation unit 14 evaluates the freshness and/or the degree of maturation of food animals, specifically computing, based on the temporal change in at least one of the K value, the FI value, or the IMP value, the storage time until at least one of the K value, the FI value, or the IMP value becomes a preset value (prescribed threshold value), or computing at least one of the K value, the FI value, or the IMP value in the food animal at a preset storage time (prescribed threshold value). Furthermore, the freshness/ degree of maturation assessment unit 15 compares the evaluation results from the freshness/degree of maturation evaluation unit 14 with a preset threshold value (prescribed threshold value) to assess the level of quality in the freshness and/or the degree of maturation in the food animal. Additionally, from these freshness/degree of maturation evaluation results and/or assessment results, information such as optimal recommended cooking information for ingredients can be displayed on the output device 3 via an internet connection or the like. Furthermore, in the case in which there has been an outbreak of an infectious disease (in particular, coronavirus disease 2019 (COVID-19), bacterial food poisoning (*Vibrio parahaemolyticus*, pathogenic *Escherichia coli, Salmonella, Campylobacter, Staphylococcus aureus*, enterohemorrhagic *Escherichia coli, Clostridium perfringens*, etc.), or viral food poisoning (norovirus, etc.)) among people associated with distribution on the distribution path, if a food animal is determined to be unsafe to eat or if considerable caution is determined to be necessary from freshness/degree of maturation evaluation results and/or assessment results and processing information based on distribution transit location information and disinfection/sterilization data, then cautionary information may be displayed on the output device 3 via an internet connection or the like. Details regarding the calculation of the change in the concentration of ATP-associated compounds by the ATP-associated compound concentration calculation unit 13, the computation of at least one of the K value, the FI value, or the IMP value by the freshness/degree of maturation evaluation unit 14, and the assessment of the freshness and/or degree of maturation of food animals by the freshness/degree of maturation assessment unit 15 will be described below.

To more specifically explain the manner of use of terminology in the present description, "evaluation" refers to indicating numerical values of freshness and degree of maturation, and "assessment" refers to determining higher/ lower relationships and distinctions by comparing the numerical values obtained by evaluation with separately set threshold values.

The data output unit 10 outputs data that needs to be transmitted to the output device 3 and data that needs to be stored in the data storage device 4 in connection with the processing in the computation device 5.

Figure 2:
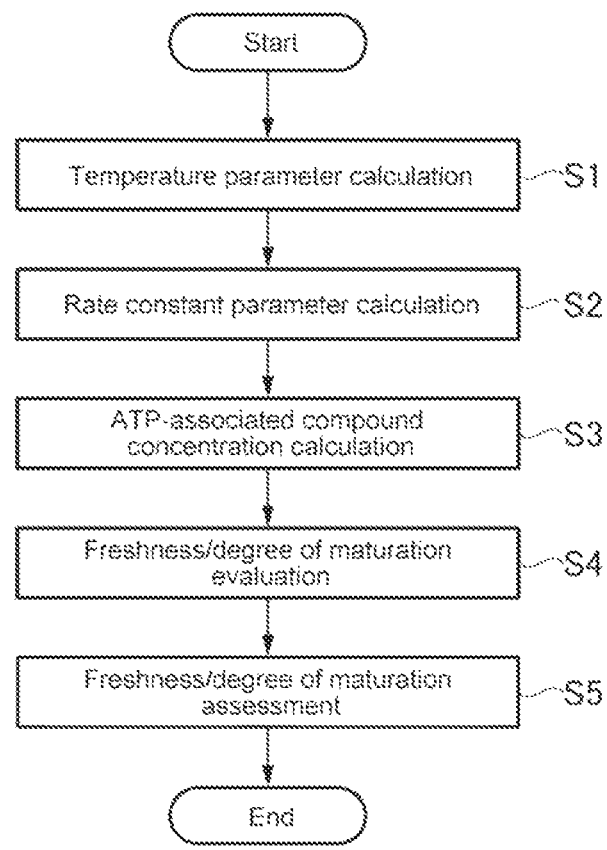
FIG. 2 is a diagram indicating the overall processing flow in the food animal freshness/degree of maturation evaluating and assessing method

Hereinafter, the freshness/degree of maturation evaluating method performed by the freshness/degree of maturation evaluating device having the above-mentioned structure will be explained. FIG. 2 is a diagram illustrating the overall processing flow in the food animal freshness/degree of maturation evaluating method. As illustrated in FIG. 2, the freshness/degree of maturation evaluating method includes processing steps that involve: the temperature parameter calculation unit 11 in the parameter calculation unit 8 calculating temperature parameters by a simulation (step S1), the rate constant calculation unit 12 in the parameter calculation unit 8 calculating rate constant parameters by a simulation (step S2), the ATP-associated compound concentration calculation unit 13 in the evaluation calculation execution unit 9 calculating ATP-associated compound concentrations by a simulation (step S3), the freshness/degree of maturation evaluation unit 14 in the evaluation calculation execution unit 9 evaluating the freshness and/or the degree of maturation (computing the K value and/or the FI value) (step S4), and the freshness/degree of maturation assessment unit 15 in the evaluation calculation execution unit 9 assessing the freshness and/or the degree of maturation of the food animal (step S5). The procedure may begin immediately at step S2 without executing step S1. In that case, step S2 is executed after registering storage temperature data from the data storage device 4 in the reading work memory 6. Hereinafter, details regarding the respective processing steps will be explained.

Figure 3:
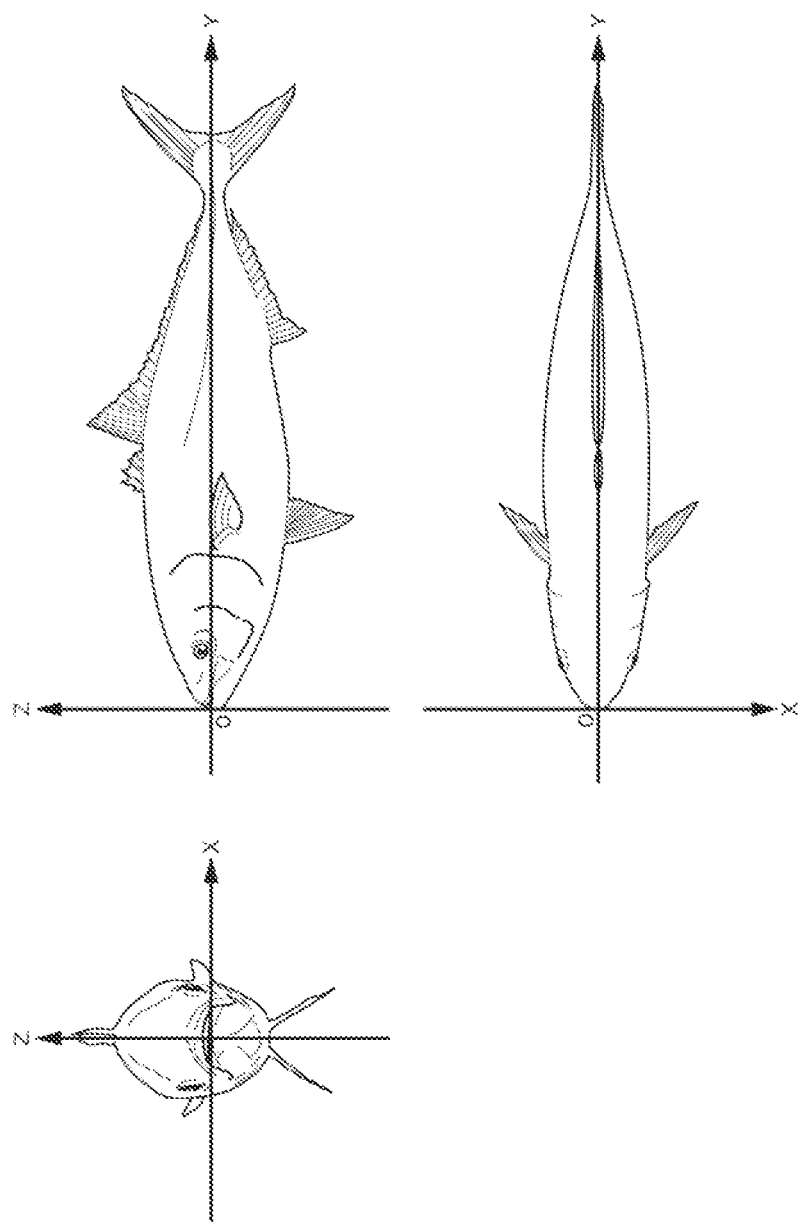
FIG. 3 is a diagram illustrating an example of an orthogonal coordinate system (origin and coordinate axes) for positions on a food animal when setting temperature parameters.

First, the temperature parameter calculation unit 11 calculates the temperature parameters in a simulation (step S1), The temperature parameter setting conditions set in step S1 will be explained by taking aquatic animals as an example among food animals. Note that there is no limitation to aquatic animals, and that embodiments with food animals are included within the technical scope of the present invention. First, in the temperature calculation parameter unit 11, data registered in the work memory 6, for example, data regarding constants necessary for solutions to unsteady heat conduction equations for each food animal species (thermal conductivity k, density p, specific heat c and generated heat Q), storage temperature, storage commencement time, size (width, length, and height) of food animal, temperature of food animal immediately before commencing storage, and position P (X coordinate, Y coordinate, Z coordinate) being calculated on the food animal, is acquired from the data storage device 4. FIG. 3 is a diagram illustrating one example of an orthogonal coordinate system (origin and coordinate axes) for the position P on a food animal in the temperature parameter settings. The coordinate system for the position P on the food animal in the present invention need not be an orthogonal coordinate system, and may be a cylindrical coordinate system, an oblique coordinate system, a polar coordinate system, or a spherical coordinate system, and embodiments obtained by appropriately combining the aforementioned coordinate systems are also included within the technical scope of the present invention.

The temperature calculation parameter unit 11 solves an unsteady heat conduction equation under boundary conditions using a data set of constants necessary for the solution to the unsteady heat conduction equation corresponding to the food animal species of interest, using the temperature of the food animal immediately before commencing storage as an initial condition, and records the temperature changes at a position P in the food animal in the work memory 6 as temperature parameters under temporal change. The present inventors measured the temperatures at arbitrary points on food animals, as a result of which they arrived at the observation that the temporal change in the temperature (temperature parameter) at that point can be expressed by a solution to an unsteady heat conduction equation.

Additionally, taking olive flounder as one example, the constants data (thermal conductivity k, density ρ, specific heat c, generated heat Q) necessary for the solution to the unsteady heat conduction equation computed on the basis of measured data were the following:

k=0.4643
ρ=999.8
c=3646.3
Q=0

Although heat is generated by the decomposition of the ATP-associated compounds, compared to the cooling for the purpose of retaining the freshness of the food animal, this heat generation is small enough to be ignored (Q=0).

Additionally, the boundary conditions used in the present invention can be decided by the heat flux between the food animal surface and the environment. If the environment is liquid or gaseous, then it is sufficient to know the environmental temperature and the thermal conductivity, and the thermal conductivity may be directly determined experimentally or estimated by heat transfer engineering.

Figure 4:
FIG. 4 is a diagram indicating an example of sequential reactions for setting rate constant parameters.

Next, the rate constant parameter calculation unit 12 calculates the rate constant parameters in a simulation (step S2). FIG. 4 is a diagram indicating an example of sequential reactions for setting rate constant parameters. The parameter setting conditions set in step S2 will be explained by using the sequential reactions indicated in FIG. 4 as an example. In the sequential reactions indicated in said diagram, ATP in a food animal generates the intermediate product ADP, which is an objective product, the intermediate product ADP generates the intermediate product AMP, which is a further objective product, the intermediate product AMP generates the intermediate product IMP, which is a further objective product, the intermediate product IMP generates HxR, which is a further objective product, and the intermediate product HxR further generates the product Hx.

If the molar concentration of ATP in the food animal is represented by C(ATP), then the reaction rate r1 from the ATP in the food animal to the intermediate product ADP at the temperature t is expressed by Expression (1) below.

$$r1 = k1 \times C(ATP) \tag{1}$$

In the above Expression (1), k1 is a reaction rate constant.

Additionally, if the molar concentration of the intermediate product ADP in the food animal is represented by C(ADP), then the reaction rate r2 from the intermediate product ADP to the intermediate product AMP is represented by Expression (2) below.

$$r2 = k2 \times C(ADP) \tag{2}$$

In the above Expression (2), k2 is a reaction rate constant.

Additionally, if the molar concentration of the intermediate product AMP in the food animal is represented by C(AMP), then the reaction rate r3 from the intermediate product AMP to the intermediate product IMP is represented by Expression (3) below.

$$r3 = k3 \times C(AMP) \tag{3}$$

In the above Expression (3), k3 is a reaction rate constant.

Additionally, if the molar concentration of the intermediate product IMP in the food animal is represented by C(IMP), then the reaction rate r4 from the intermediate product IMP to the intermediate product HxR is represented by Expression (4) below.

$$r4 = k4 \times C(IMP) \tag{4}$$

In the above Expression (4), k4 is a reaction rate constant.

Additionally, if the molar concentration of the intermediate product HxR in the food animal is represented by C(HxR), then the reaction rate r5 from the intermediate product HxR to the product Hx is represented by Expression (5) below.

$$r5 = k5 \times C(HxR) \tag{5}$$

In the above Expression (5), k5 is a reaction rate constant.

Next, the molar concentrations of the respective components corresponding to reaction times (storage times) at prescribed time intervals in the sequential reactions in FIG. 4 are estimated. Specifically, simultaneous ordinary differential equations are established by associating the above-mentioned reaction rate expressions in Expression (1) to Expression (5) with Expression (6) to Expression (11) defined below. By numerically integrating these equations, the molar concentrations of the respective components can be successively estimated.

$$dC(ATP)/dt = -r1 \tag{6}$$

$$dC(ADP)/dt = r1 - r2 \tag{7}$$

$$dC(AMP)/dt = r2 - r3 \tag{8}$$

$$dC(IMP)/dt = r3 - r4 \tag{9}$$

$$dC(HxR)/dt = r4 - r5 \tag{10}$$

$$dC(Hx)/dt = r5 \tag{11}$$

The rate constant parameters are determined by the following method. First, measured values (documented values or measured values stored in the data storage device 4) of the ATP-associated reaction product concentration changes at two or more different storage temperatures in the same food animal species are referenced, and measured values of the concentrations of the respective components for each of the storage times and storage temperatures are acquired. Next, at the above-mentioned storage temperatures, arbitrary initial values for the rate constants are substituted into k1 k2, k3, k4, and k5, thereby defining the reaction rate expressions of Expression (1) to Expression (5) above and the next Expression (6) to Expression (11) to establish simultaneous ordinary differential equations, and these equations are numerically integrated to estimate the molar concentrations of the respective components. The sums of the squares of the differences between the molar concentrations of the respective components for the cases in which the measured values and the arbitrary rate constants are used at the aforementioned storage temperatures are determined, and the respective rate constants at the respective storage temperatures are determined by changing the values of the rate constants so that the sums of the squares of the differences are minimized. In a non-linear planning problem in which the rate constant parameters of concentration changes are to be decided, the generalized reduced gradient method, an evolutionary method or the like may be appropriately selected and used.

If the reaction rate constants at two or more different storage temperatures in the same food animal species can be determined, then it becomes possible to compute a relational expression between the respective rate constants of the sequential reactions and the temperatures at arbitrary temperatures with respect to the food animal species. The relational expression between the respective rate constants of the sequential reactions and the temperatures may be a linear polynomial (first-order expression) or a polynomial interpolation, which may be appropriately selected and used.

In this way, rate constant parameters that minimize the sums of squares, i.e., the rate constant parameters k1, k2, k3, k4, and k5 that best fit the measured data, are determined, and the reaction rate expressions are defined. Furthermore, these can be used to define relational expressions between the temperatures and the reaction rate expressions. Relational expressions between rate constants and temperatures making combined use of linear polynomials (first-order expressions) and polynomial interpolations regarding the reaction temperatures and the rate constants computed on the basis of the measured data in Non-Patent Document 4, using olive flounder as an example, are indicated below, $$k1 = 0.0018 \times t + 0.0647 \tag{12}$$

$$k2 = 0.0192 \times t^2 + 0.1788 \times t + 0.4279 \tag{13}$$

$$k3 = -0.0123 \times t^2 + 0.0643 \times t + 0.8286 \tag{14}$$

$$k4 = 0.0001 \times t^2 - 0.0002 \times t + 0.0017 \tag{15}$$

$$k5 = 0.002 \times t + 1.2874 \tag{16}$$

In Expression (12) to Expression (16) above, t represents the storage temperature (° C.).

The above relational expressions between the temperatures and the respective rate constants of the sequential reactions are pre-stored in the data storage device 4 for each food animal species, and appropriate relational expressions for the rate constants may be computed based on food animal species information selected at the input unit 2 and temperature parameters computed by the reaction temperature parameter calculation unit 11 in step S1, or relational expressions between the temperatures and the rate constants may be calculated each time, in accordance with step S2, based on measured data regarding ATP-associated compound concentrations pre-stored in the data storage device 4 for each food animal species. The process may be started immediately at step S2 without executing step S1. In that case, step S2 is executed after registering the storage temperature data from the data storage device 4 in the reading work memory 6. By making the respective rate constants appropriately vary in accordance with the storage time, simulation results that fit more closely with measured values can be obtained.

Furthermore, an ATP-associated compound concentration calculation is performed by the ATP-associated compound concentration calculation unit 13 (step S3). In step S3, based on the temperature parameters selected in step S1 and the relational expressions for the rate constants selected in step S2, specifically, by defining the reaction rate expressions of Expression (1) to Expression (5) above and Expression (6) to Expression (11), simultaneous ordinary differential equations are established, and these are numerically integrated, thereby estimating the sequential temporal changes in molar concentrations of the respective components. As the numerical integration method, the Runge-Kutta method, the Runge-Kutta-Gill method, Euler's method, Gears method, etc. may be appropriately selected and used. Additionally, by accumulating data for the same species that have been similarly determined, machine learning or the like may be implemented on the basis of the accumulated data in the data storage device 4, thereby raising the precision of the data set.

Furthermore, in the explanation above, an ATP-associated compound concentration calculation computation method relating to sequential reactions, in which the sequential reactions were the five steps ATP→ADP, ADP→AMP, AMP→IMP, IMP→HxR, and HxR→Hx, was explained. However, the ATP-associated compound concentration may be determined for sequential reactions having two or more steps. In this case, the ATP-associated compound concentration calculation computation method regarding the two-step sequential reactions indicated in FIG. 5, ATP+ADP+AMP→IMP and IMP→HxR+Hx, will be explained below.

If the molar concentration obtained by summing the respective concentrations of ATP, ADP, and AMP in a food animal is represented by C(ATP+ADP+AMP), then the reaction rate r6 from the total of ATP, ADP, and AMP to the intermediate product IMP in the food animal, at a certain storage temperature t (° C.), is expressed by Expression (17) below.

$$r6 = k6 \times C(ATP+ADP+AMP) \tag{17}$$

In Expression (17) above, k6 is a reaction rate constant.

Additionally, if the molar concentration of the intermediate product IMP in the food animal is represented by C(IMP), then the reaction rate r7 from the intermediate product IMP to the product (total of HxR and Hx) is expressed by Expression (18) below, $$r7 = k7 \times C(IMP) \tag{8}$$

In Expression (18) above, k7 is a reaction rate constant.

Figure 5:
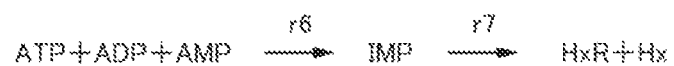
FIG. 5 is a diagram indicating an example of sequential reactions for setting rate constant parameters.

Next, the molar concentrations of the respective components corresponding to storage times at prescribed time intervals in the sequential reactions in FIG. 5 are estimated. Specifically; simultaneous ordinary differential equations are established by associating the above-mentioned reaction rate expressions in Expression (17) and Expression (18) with Expression (19) to Expression (21) defined below; and the analytical solutions in Expression (22) to Expression (24) are obtained.

$$dC(ATP+ADP+AMP)/dt = -r6 \tag{19}$$

$$dC(IMP)/dt = r6 - r7 \tag{20}$$

$$dC(HxR+Hx)/dt = r7 \tag{21}$$

$$[ATP+ADP+AMP] = [ATP+ADP+AMP]_0 \times \exp(-k6 \times t) \tag{22}$$

$$[IMP] = \{k6 \times [ATP+ADP+AMP]_0/(k7-k6)\} \times (\exp(-k6 \times t) \exp(-k7 \times t)) \tag{23}$$

$$[HxR+Hx] = [ATP+ADP+AMP]_0 \times [1 - \{k7 \times \exp(-k6 \times t) - k6 \times \exp(-k7 \times t)\}/(k7-k6)] \tag{24}$$

$[ATP+ADP+AMP]_0$ represents the total initial concentration of ATP, ADP, and AMP, t represents the storage time, $[ATP+ADP+AMP]$ represents the total concentration of ATP, ADP, and AMP at the storage time t, and [IMP] and [HxR Hx] respectively represent the concentrations of IMP and the total of HxR and Hx at the storage time t. In other words, in the case in which Expression (22) to Expression (24) are used, the respective concentrations can be computed, without using a numerical integration method, by directly substituting the storage times into t.

Additionally, the reaction rate expressions are established by determining the rate constant parameters k6 and k7 so as to be the rate constant parameters that minimize the sums of the squares to best fit the measured data. Furthermore, these can be used to establish relational expressions between the temperatures and the reaction rate expressions.

The number of the rate constant parameters is not particularly limited. However, considering the increases in calculation errors and number of steps in parameter determination work, there should preferably be ten or fewer, and for the purposes of increasing calculation precision, there should be five or fewer, and more preferably two. The reason for this is because, since the respective rate constants are determined at the respective storage temperatures by changing the values of the rate constants so that the value of the sum of the squares of the differences in the measured data are minimized, if the number of rate constant parameters is greater than ten, then the number of combinations of parameters becomes large, thus requiring more time for computation work, and the uniqueness of the solution cannot be ensured, so that multiple combinations become possible. Additionally, due to the number of parameters becoming large, the error in the numerical integration calculations also becomes large. However, if there are two rate constant parameters, then a solution is obtained, not only by numerical analysis, but also analytically, thereby eliminating the error, and the parameters can also be determined in a short time.

Next, a freshness/degree of maturation evaluation is performed by the freshness/degree of maturation evaluation unit 14 (step S4). In step S4, the freshness/degree of maturation evaluation unit 14 computes the temporal change in the K value and/or the FI value based on the simulated values of the ATP-associated compound concentrations calculated in step S3. Additionally, the freshness/degree of maturation evaluation unit 14 can, based on the temporal change in at least one value among the K value, the FI value, or the IMP value, compute the storage time until at least one of the K value, the FI value, or the IMP value becomes a preset value (prescribed threshold value), or at least one of the K value, the FI value, or the IMP value at a set storage time (prescribed threshold value), thereby allowing backwards computation of the time and the month and day on which a fish should be caught and commence being transported. Additionally, this calculated evaluation information can be sent to the data output unit 10 as needed.

Finally, a freshness/degree of maturation assessment is performed by the freshness/degree of maturation assessment unit 15 (step S5). In step S5, the freshness/degree of maturation unit 15 assesses the level of quality of the freshness and/or the degree of maturation of the food animal by comparing the evaluation result by the freshness/degree of maturation evaluation unit 14 with a preset threshold value (prescribed threshold value). For example, the maximum value of a certain specific component (for example, the IMP value, which is an umami component), is detected by the freshness/degree of maturation evaluation unit 14 in advance. Next, the freshness/degree of maturation assessment unit 15 uses a designated assessment criterion (prescribed threshold value) to assess the degree of maturation at a certain storage time. Furthermore, the freshness/degree of maturation assessment unit 15 may compute necessary conditions, such as optimized preservation temperatures and preservation times, based on these computation results, and may automatically input these as transportation conditions when an order is placed. The threshold value (prescribed threshold value) used for the comparison may be arbitrarily set by a user of the present device. Additionally, this calculated evaluation information is sent to the data output unit 10 as needed. While there are various definitions of degree of maturation, in this case, as one example, the degree of maturation of a food animal at the storage time T is defined by the following Expression (25).

Degree of maturation (%) at storage time $T$=(concentration of umami component(IMP value) at storage time $T$÷maximum concentration of umami component(maximum IMP value))×100 (25)

The assessment method based on Expression (25) is merely one example, and the actual degree of maturation assessment criterion (prescribed threshold value) may be arbitrarily set by a user of the present device. For example, it is possible to determine that maturation has been achieved at the stage at which the concentration of the IMP value becomes a certain threshold value, without using Expression (25).

Furthermore, the level of quality in the freshness and/or degree of maturation of a food animal can be assessed based on the relationship between the IMP value and the K value and/or the FI value.

Additionally, from the assessment results by the freshness/degree of maturation assessment unit 15, information such as optimal recommended cooking information for ingredients can be displayed on the output device 3 via an internet connection or the like. Furthermore, in the case in which there has been an outbreak of an infectious disease (in particular, coronavirus disease 2019 (COVID-19), bacterial food poisoning (*Vibrio parahaemolyticus*, pathogenic *Escherichia coli*; *Salmonella*, *Campylobacter*, *Staphylococcus aureus*, enterohemorrhagic *Escherichia coli*, *Clostridium perfringens*, etc.), or viral food poisoning (norovirus, etc.)) among people associated with distribution on the distribution path, if a food animal is determined to be unsafe to eat or if considerable caution is determined to be necessary based on the freshness/degree of maturation assessment results and processing information based on fishery-, slaughter-, processing-, market-, and distribution-associated person data, distribution transit location information and disinfection/sterilization data, then cautionary information may be displayed on the output device 3 via an internet connection or the like.

Example 1

As the present example, an example in which the freshness/degree of maturation evaluating device 1 is used to compute ATP-associated compound concentrations, K values and FI values in olive flounder will be explained.

Figure 6:
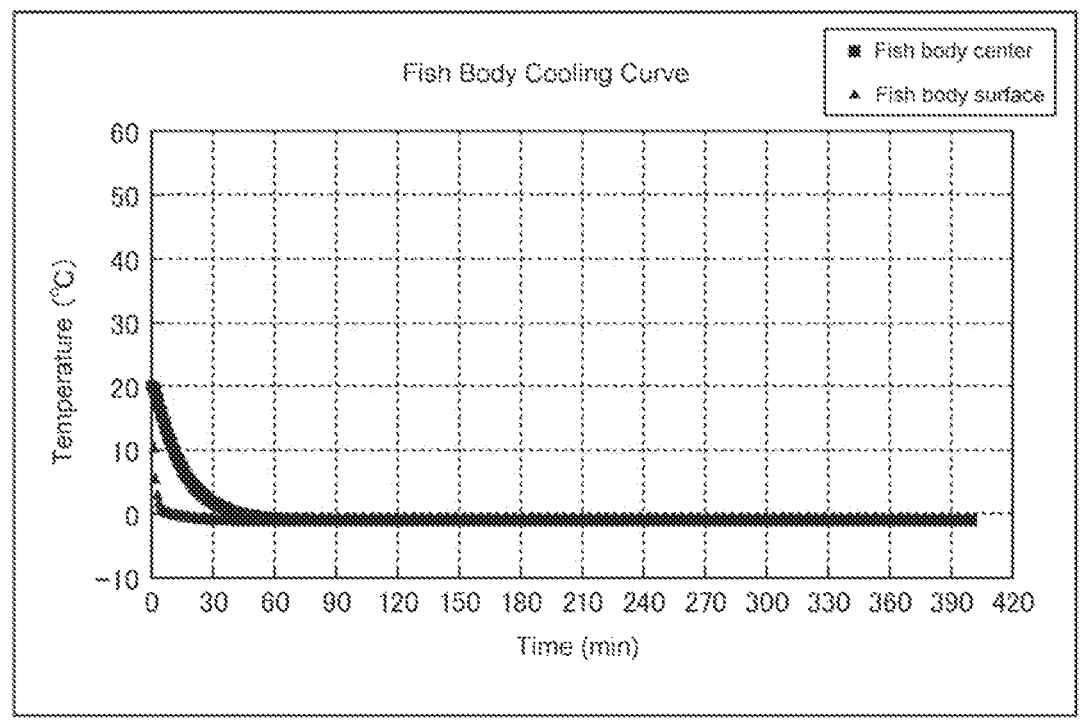
FIG. 6 is a diagram indicating an example of the results of a cooling process at a surface portion and at a central portion of an olive flounder when the storage temperature is 0° C.
Figure 7:
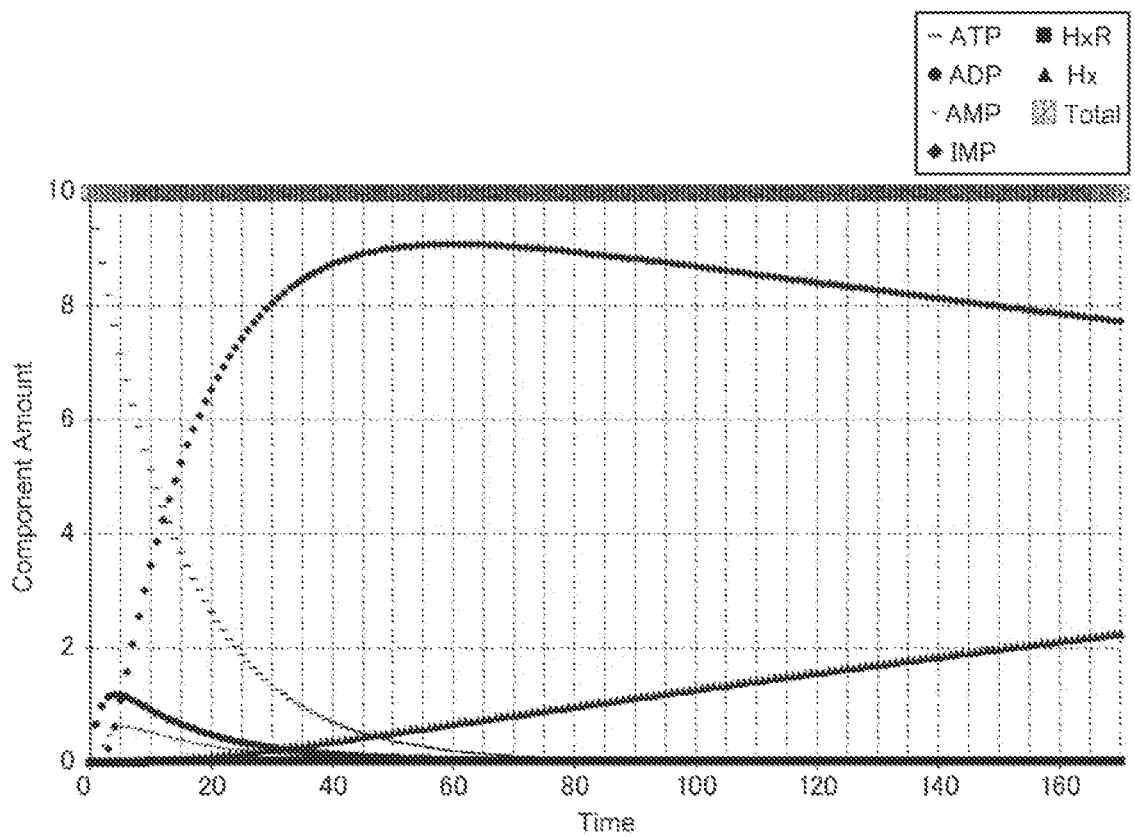
FIG. 7 is a diagram indicating an example of simulation results for ATP-associated compound concentrations at a storage temperature of 0° C.
Figure 8:
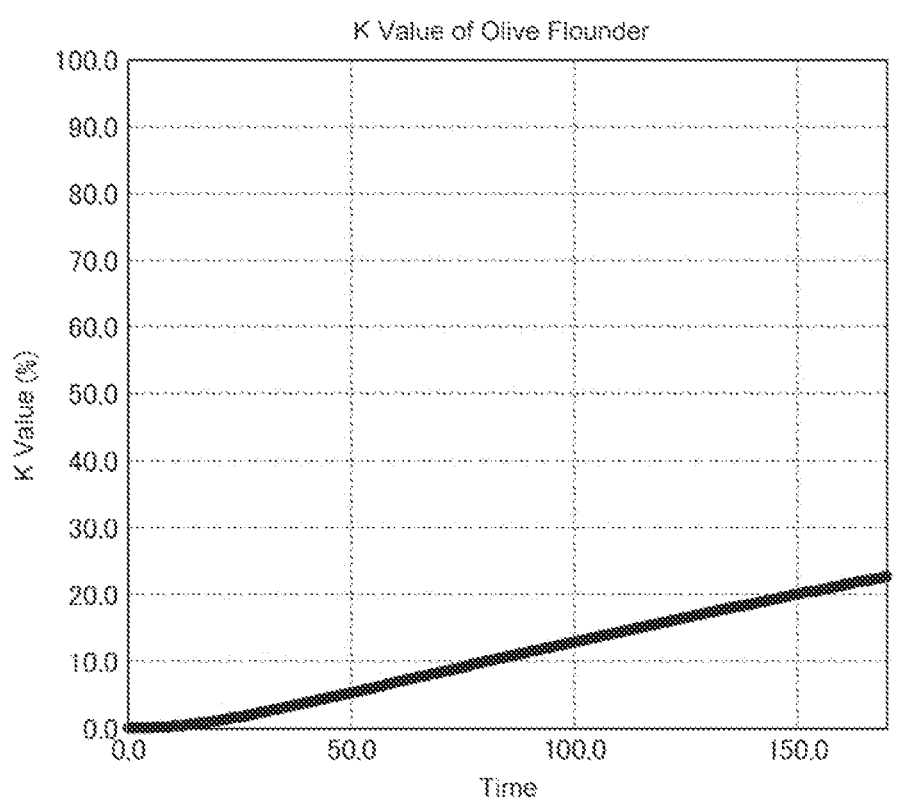
FIG. 8 is a diagram indicating an example of simulation results for K values at a storage temperature of 0° C.
Figure 9:
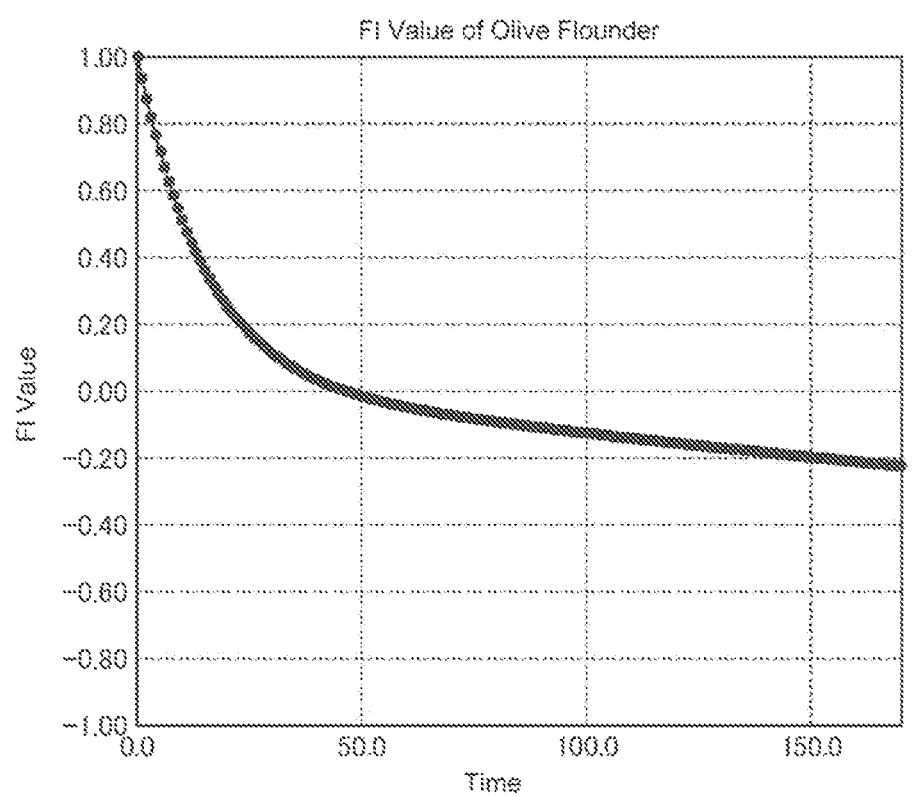
FIG. 9 is a diagram indicating an example of simulation results for FI values at a storage temperature of 0° C.

The case in which the above-mentioned Expression (12) to Expression (16) are used as relational expressions between the storage temperatures and various rate constants in olive flounder using the freshness/degree of maturation evaluating device 1, and the above-mentioned constants data for olive flounder (k=0.4643, ρ=999.8, c=3645.3, Q=0) are used as the constants data necessary for the solution to the unsteady heat conduction equation and is pre-stored in the data storage device 4 will be described. FIG. 6 is a diagram indicating an example of the results of a cooling process at a surface portion and at a central portion of an olive flounder when the storage temperature is set to 0° C. FIG. 6 shows the results of a cooling process (in this case, the values for a storage time of 0 minutes to 400 minutes) at the fish body center P (0, 20, 0) and the fish body surface P (1.5, 20, 0)

when the temperatures at the surface and at the center of the olive flounder immediately before commencing storage were 20° C., the olive flounder had a width (X coordinate) of 3 cm, a length (Y coordinate) of 40 cm, and a height (Z coordinate) of 40 cm, the initial ATP molar concentration was 10 µm/g, the storage time was 170 hours, and the storage temperature was 0° C. FIG. 7 is a diagram indicating an example of simulation results for ATP-associated compound concentrations at a storage temperature of 0° C. FIG. 7 shows the relationship between the storage time and the change in the ATP-associated compound concentrations using temperature parameters at the fish body center P (0, 20, 0). FIG. 8 is a diagram indicating an example of simulation results for K values at a storage temperature of 0° C. FIG. 9 is a diagram indicating an example of simulation results for FI values at a storage temperature of 0° C. FIG. 8 shows the relationship between the storage time and K values, and FIG. 9 shows the relationship between the storage time and FI values.

Figure 10:
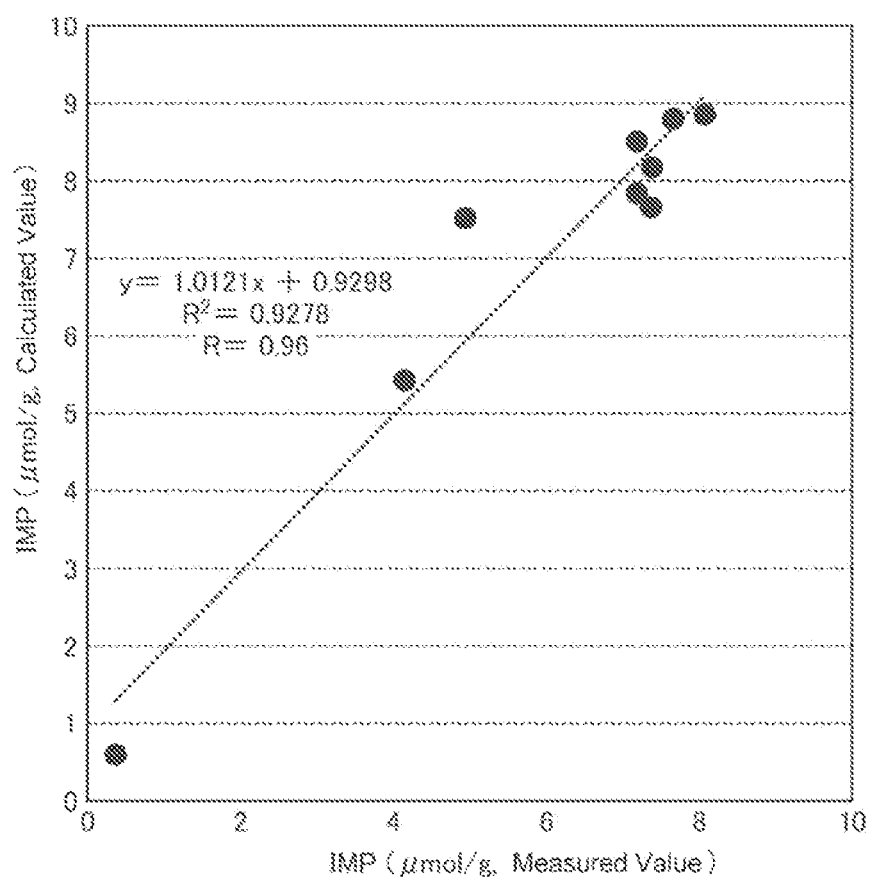
FIG. 10 is a diagram indicating a comparative example of measured values (see Non-Patent Document 4) and simulated values, at the same storage times, for IMP values at a storage temperature of 0° C.

According to the cooling curve in FIG. 6, the temperature at the fish body center P (0, 20, 0) of the olive flounder became 0° C. after approximately 60 minutes. Among the ATP-associated compound concentrations in FIG. 7 computed by using this temperature parameter, for example, the IMP value used for evaluating and determining the degree of maturation, when comparing measured values (see Non-Patent Document 4) with simulated values at the same storage times, as indicated in FIG. 10, the correlation coefficient (R) was 0.96, which is a reasonable value. FIG. 10 is a diagram indicating a comparative example between measured values (see Non-Patent Document 4) and simulated values, at the same storage time, for IMP values at a storage temperature of 0° C. Among the measured values in Examples 1 to 26, for measured values in which the killing times or slaughter times are not the same as the storage commencement times (i.e., in which the K value at a storage time of 0 hours is a non-zero measured value), the respective measurement points were corrected to make the K value be zero at a storage time of 0 hours. However, the corrections are only about a few hours with respect to the overall evaluation time, and they were confirmed in advance to have no impact on the evaluation results.

Example 2

Figure 11:
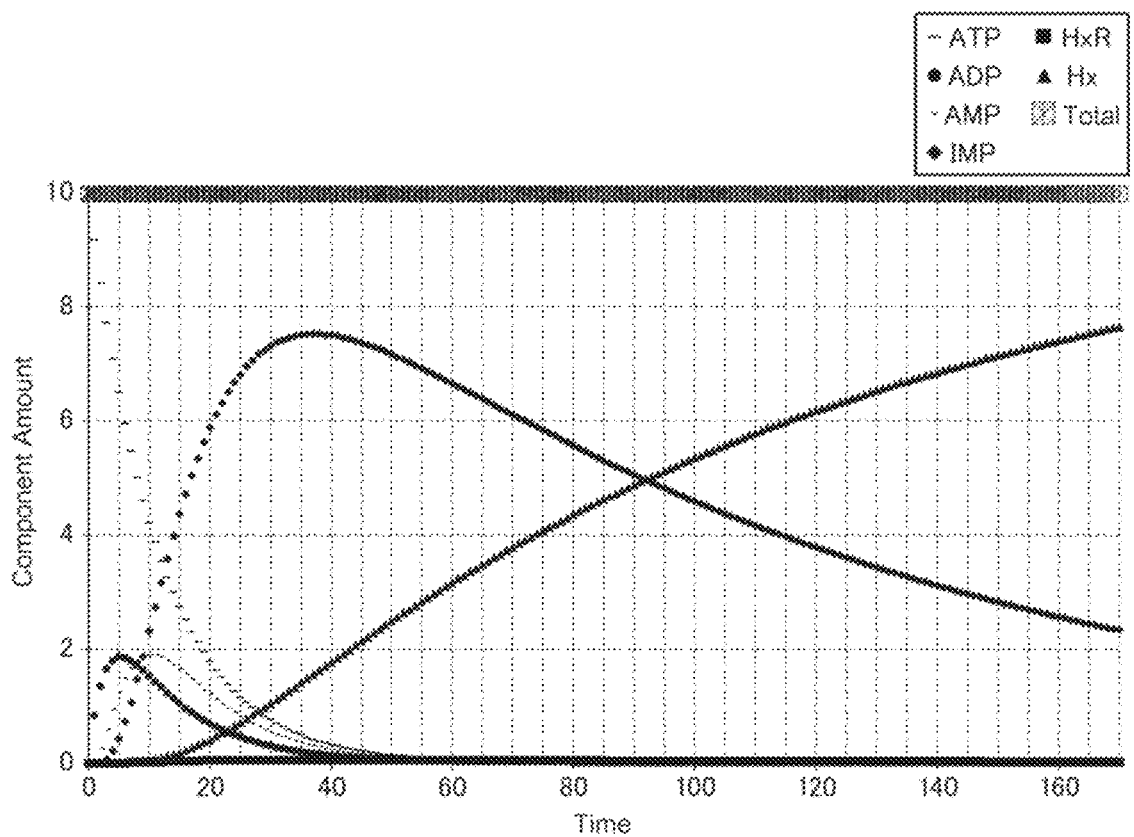
FIG. 11 is a diagram indicating an example of simulation results for ATP-associated compound concentrations at a storage temperature of 10° C.
Figure 12:
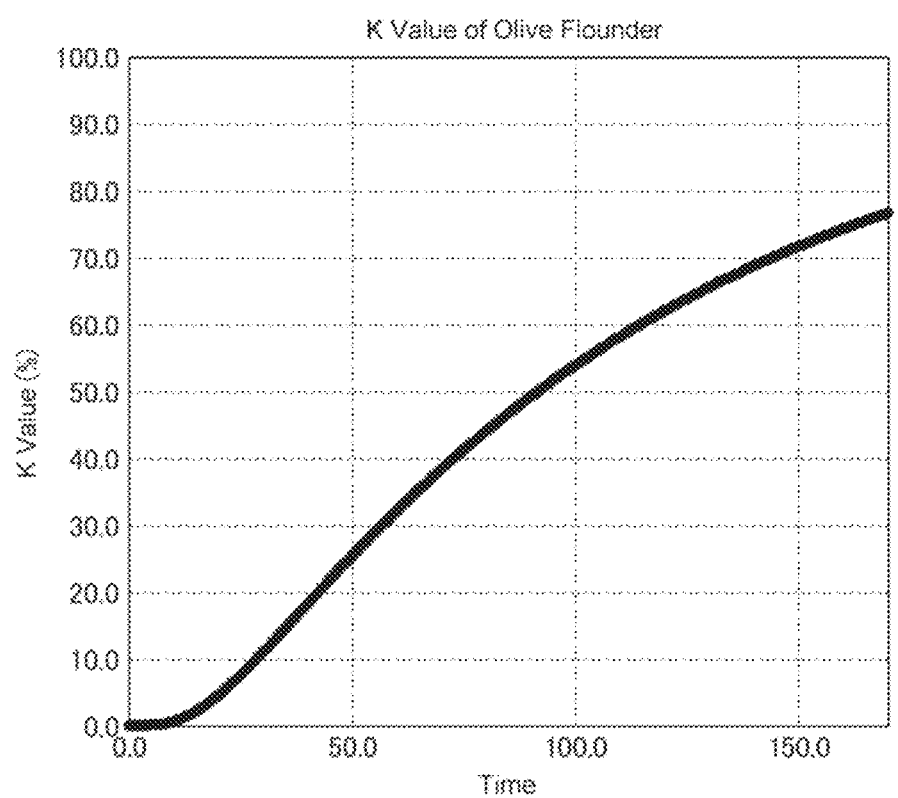
FIG. 12 is a diagram indicating an example of simulation results for K values at a storage temperature of 10° C.
Figure 13:
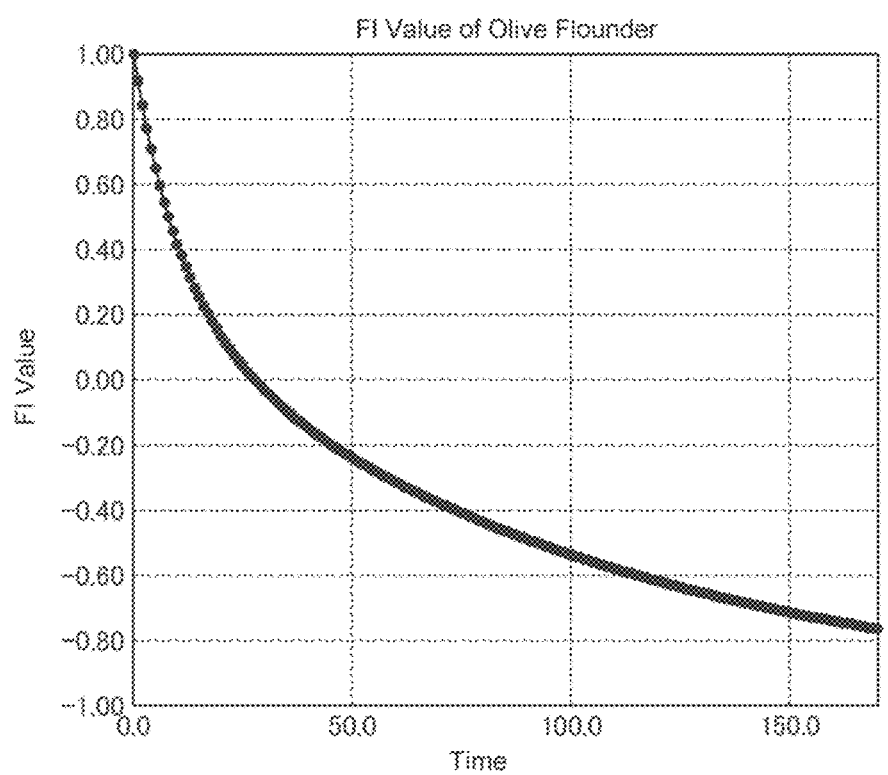
FIG. 13 is a diagram indicating an example of simulation results for FI values at a storage temperature of 10° C.

Next, the ATP-associated compound concentrations, the K values, and the FI values at the fish body center P (0, 20, 0) were computed by the same method as that in Example 1 above, except that the storage temperature was changed to 10° C. The relationship between the storage time and the changes in the ATP-associated compound concentrations is shown in FIG. 11, the relationship between the storage time and the K values is shown in FIG. 12, and the relationship between the storage time and the FI values is shown in FIG. 13. FIG. 11 is a diagram indicating an example of simulation results for ATP-associated compound concentrations at a storage temperature of 10° C., FIG. 12 indicates the simulation results for K values at a storage temperature of 10° C., and FIG. 13 indicates the simulation results for FI values at a storage temperature of 10° C.

Figure 14:
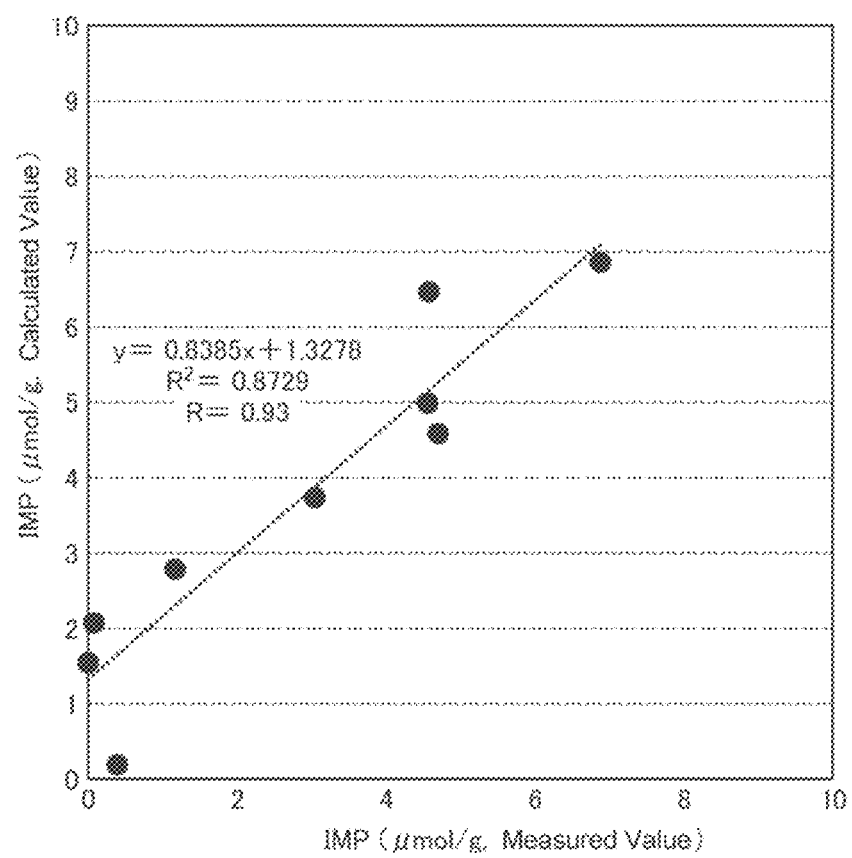
FIG. 14 is a diagram indicating a comparative example of measured values (see Non-Patent Document 4) and simulated values, at the same storage times, for IMP values at a storage temperature of 10° C.

FIG. 14 is a diagram indicating a comparative example between measured values (see Non-Patent Document 4) and simulated values, at the same storage times, for IMP values at a storage temperature of 10° C. Among the ATP-associated compound concentrations indicated in FIG. 11, for example, the IMP values used for evaluating and determining the degree of maturation, when comparing measured values (see Non-Patent Document 4) with simulated values at the same storage times, as indicated in FIG. 14, the correlation coefficient (R) was 0.93, which is a reasonable value.

Figure 15:
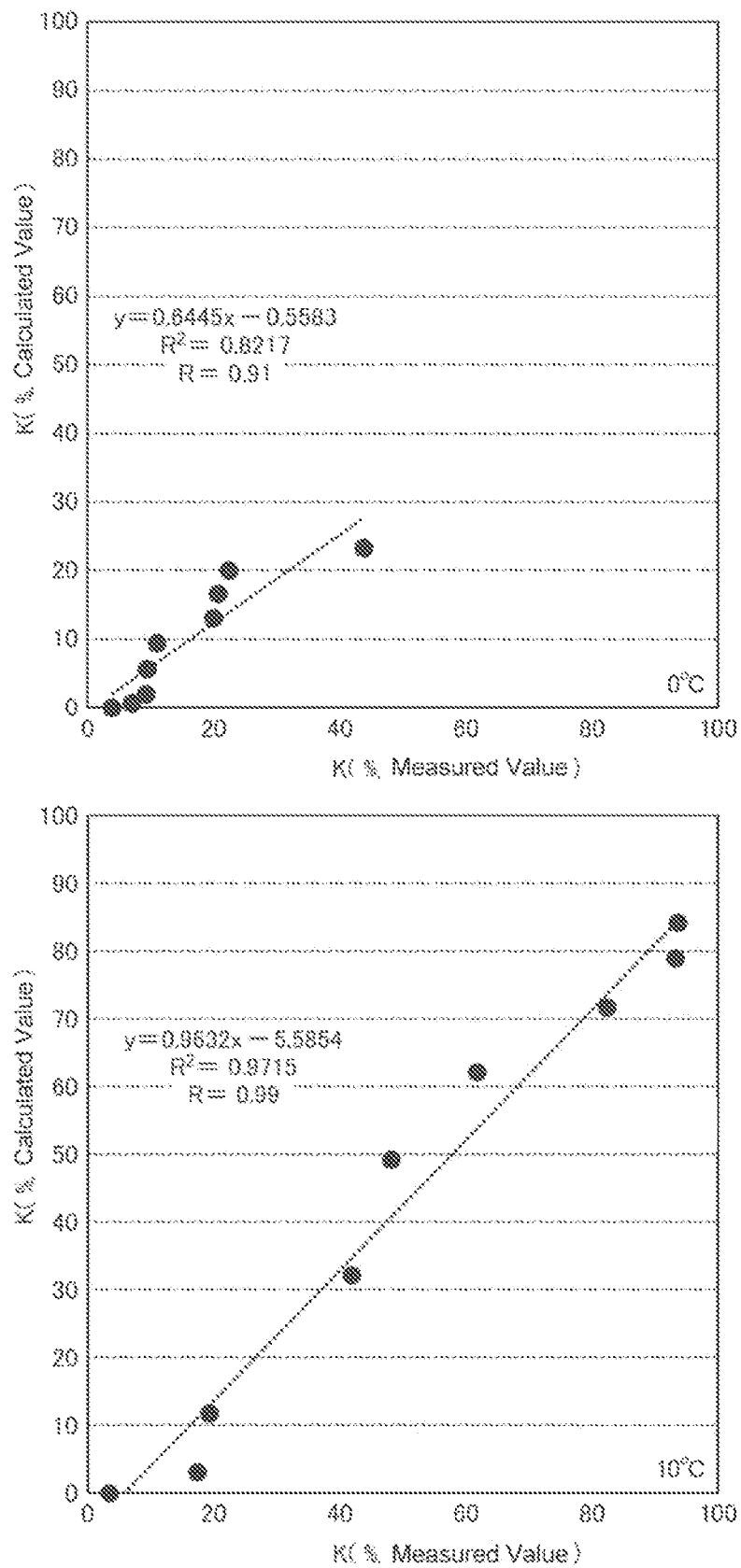
FIG. 15 is a diagram indicating a comparative example of measured and simulated K values.

FIG. 15 is a diagram indicating a comparative example between measured (see Non-Patent Document 4) and simulated K values. FIG. 15 shows a comparison between measured and simulated K values at the same storage times, at the fish body center P (0, 20, 0), in Example 1 and Example 2 above. The correlation coefficient (R) between the simulated values and the measured values (see Non-Patent Document 4) of the K values was approximately 0.91 at a storage temperature of 0° C., and was approximately 0.99 at a storage temperature of 10° C., which are reasonable values.

Figure 16:
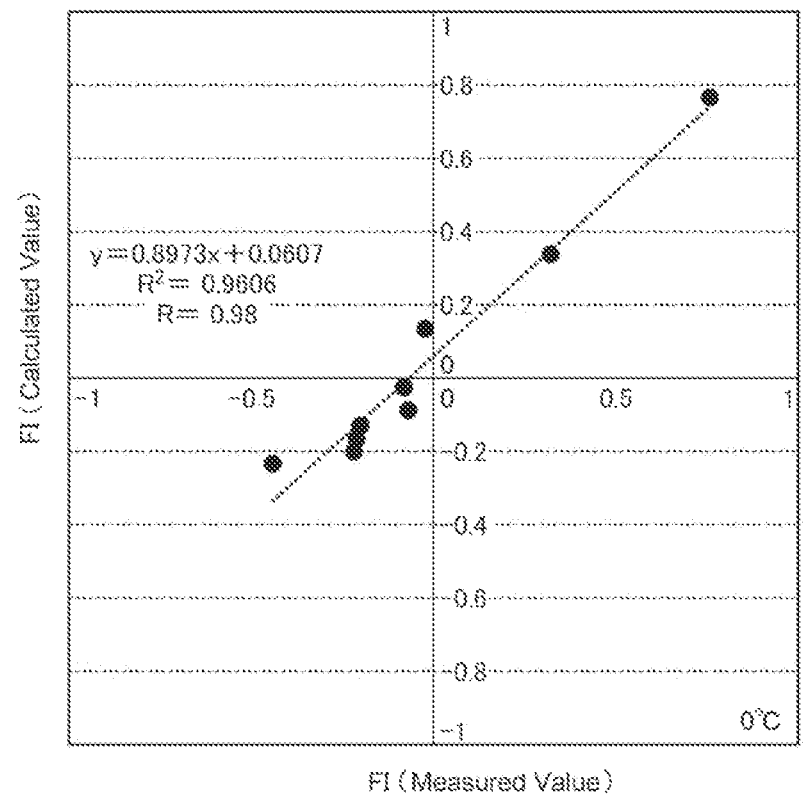
FIG. 16 is a diagram indicating a comparative example of measured and simulated FI values.
Figure 16:
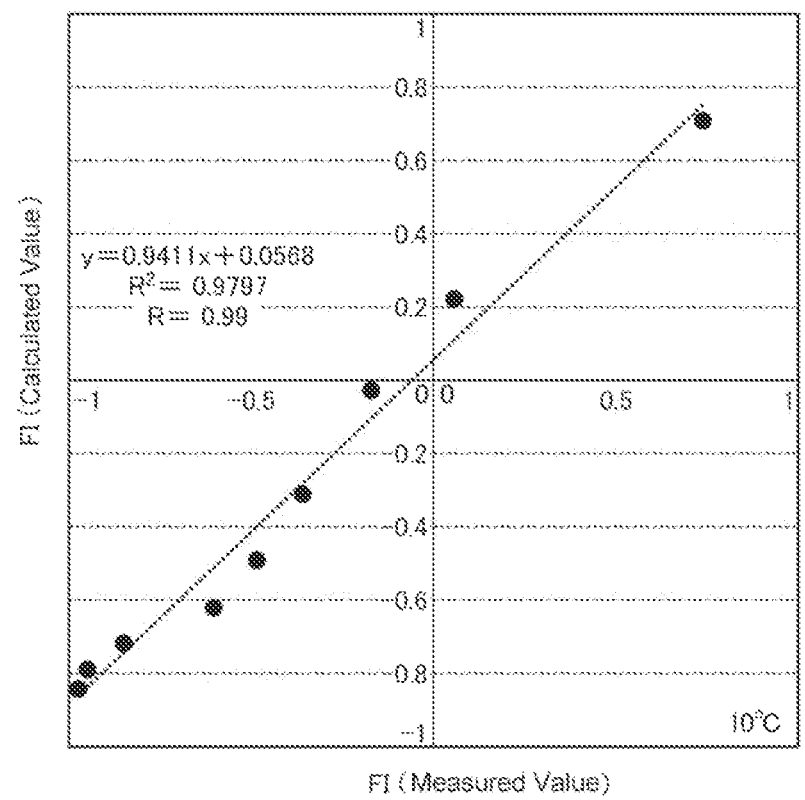

FIG. 16 is a diagram indicating a comparison between measured (see Non-Patent Document 4) and simulated FI values. FIG. 16 shows a comparison between measured and simulated FI values at the same storage times, at the fish body center P (0, 20, 0), in Example 1 and Example 2 above. The correlation coefficient (R) between the simulated values and the measured values of the FI values was approximately 0.98 at a storage temperature of 0° C., and was approximately 0.99 at a storage temperature of 10° C., which are reasonable values.

Figures 17, 18:
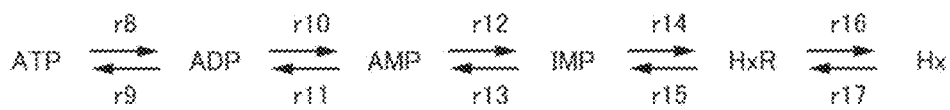
FIG. 17 is a diagram illustrating an example of a screen on which freshness evaluation and degree of maturation calculation results have been output.
FIG. 18 is a diagram indicating an example of sequential reactions for setting rate constant parameters.

FIG. 17 is a diagram illustrating an example of a screen for outputting freshness evaluations and degree of maturation calculation results, which is one example of an output screen for evaluation results using K values, FI values, and IMP values at the fish body center P (0, 20, 0) at a storage temperature of 10° C. For example, in an assessment using K values, the storage time that is optimal for flavorful eating can be determined by using FIG. 11 and FIG. 12 to compute the storage time at which the IMP value is the maximum value with the K value lower than 20. Additionally, a K value of 20 is the upper limit value serving as a criterion of suitability for raw consumption, and the storage time at which this value is reached can be computed. Meanwhile, in an assessment using FI values, for example, in the case in which a consumer has designated a value of 0 or higher as the FI value that is optimal for flavorful eating, the time at which the IMP value becomes the maximum under these conditions can be computed from FIG. 11 and FIG. 13, and the storage time corresponding to that time can be determined. Additionally, in the case that the consumer, for example, has determined to refrain from raw consumption when the FI value is −0.2, a computation of the storage time corresponding to that time and an assessment regarding whether or not consumption is possible may be displayed. Furthermore, the degree of maturation (%) can be computed by using the aforementioned Expression (25), and as an example, the IMP value data in FIG. 11 shows that the degree of maturation (%) is 88.73% after a storage time of 24 hours. Thus, the degree of maturation (%) at an arbitrary storage time can be determined. In this way, the K values, the FI values or the degrees of maturation (%) at actual times necessary at distribution sites can be computed, and the freshness can be displayed and assessed in real time. These assessment criteria are criteria that can be arbitrarily set by a user of the present device, and the present device can assess freshness and degree of maturation based on the set criteria (prescribed threshold values).

The above results demonstrate that freshness predictions using simulations are possible without actually measuring food animals during the distribution process, and that, by extracting only the necessary component information and predicting the temporal changes therein, evaluations by evaluation indices using the necessary components and computations of the degree of maturation are possible.

Example 3

Next, an example for the case in which the parameter setting conditions set in step S2 have been applied to the sequential reactions indicated in FIG. 18 has been indicated. Specifically, ATP-associated compound concentrations were determined for the five steps ATP→ADP, ADP→AMP, AMP→IMP, IMP→HxR, and HxR→Hx, while also taking into consideration the reverse reactions. The K values, the FI values, and the changes in the ATP-associated compound concentrations at the center P (0, 7.5, 0), with a storage temperature of 15° C., for a storage time of 96 hours, with an initial ATP molar concentration of 7.5 μm/g, were determined by using, as the constants data necessary for the solution to the unsteady heat conduction equation, the average values (k=0.4277, ρ=999.8 c=3564.2, Q=0) for thirteen common fish species, and with a sweetfish having a width (X coordinate) of 3 cm, a length (Y coordinate) of 15 cm, and a height (Z coordinate) of 4 cm, with the temperatures at the surface and at the center of the sweetfish immediately before commencing storage being 20° C. Although the FI values can also be computed by the changes in the ATP-associated compound concentrations, since the K values and the FI values can be converted between each other, the K values will be described in detail as representative values in subsequent examples. The reaction rates used in this case, which were reaction rates determined so as to minimize the error between measured values and calculated values, were; r8=1.0000, r9=0.2000, r10=0.7000, r11=0, r12=0.7000, r13=0, r14=0.0110, r15=0, r16=0.0200, and r17=0.

Example 4

Next, ATP-associated compound concentrations and K values at the fish body center P (0, 7.5, 0) were computed by the same method as that in Example 3 above, aside from the fact that an ATP-associated compound concentration calculation computation method relating to the five-step sequential reactions ATP→ADP, ADP→AMP, AMP→IMP, IMP→HxR, and HxR→Hx indicated in FIG. 4, as the sequential reactions, was used. As the respective reaction rates, r1=1.0000, r2=0.7000, r3=0.7000, r4=0.0110, and r5=0.0200 were used.

Example 5

ATP-associated compound concentrations and K values at the fish body center P (0, 7.5, 0) were computed by the same method as that in Example 3 above, aside from the fact that an ATP-associated compound concentration calculation computation method relating to the two-step sequential reactions ATP+ADP+AMP→IMP and IMP→HxR+Hx indicated in FIG. 5, as the sequential reactions, was used. As the respective reaction rates, r6=0.5000 and r7=0.0109 were used.

Figure 19:
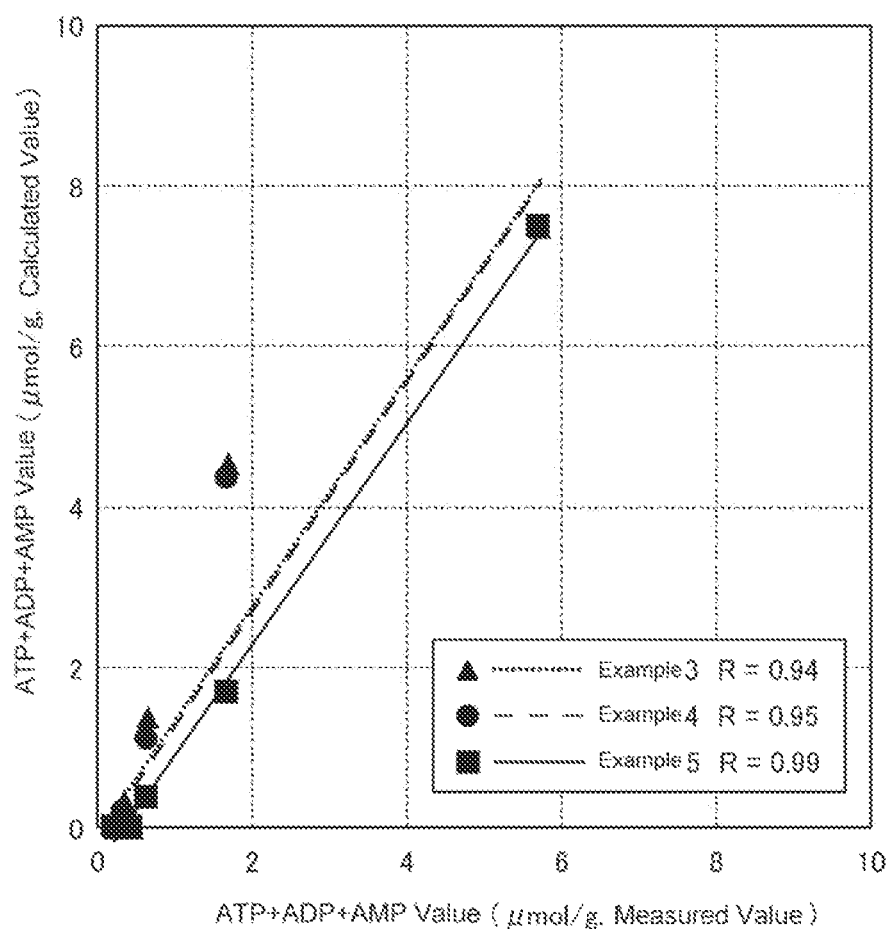
FIG. 19 is a diagram indicating a comparative example of measured and simulated ATP+ADP+AMP values in sweetfish at a storage temperature of 15° C.
Figure 20:
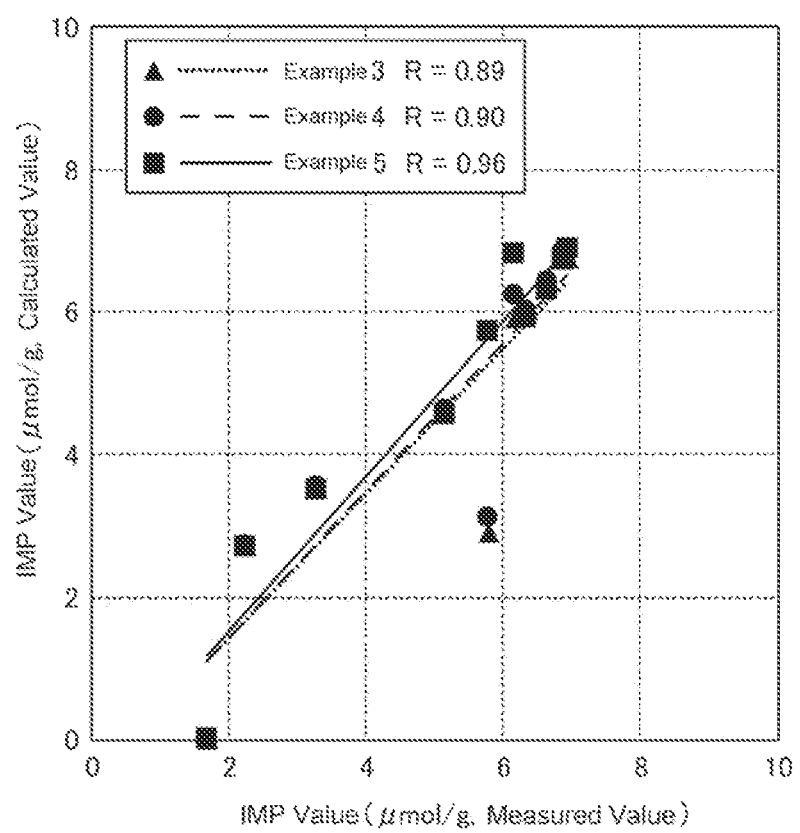
FIG. 20 is a diagram indicating a comparative example of measured and simulated IMP values in sweetfish at a storage temperature of 15° C.
Figure 21:
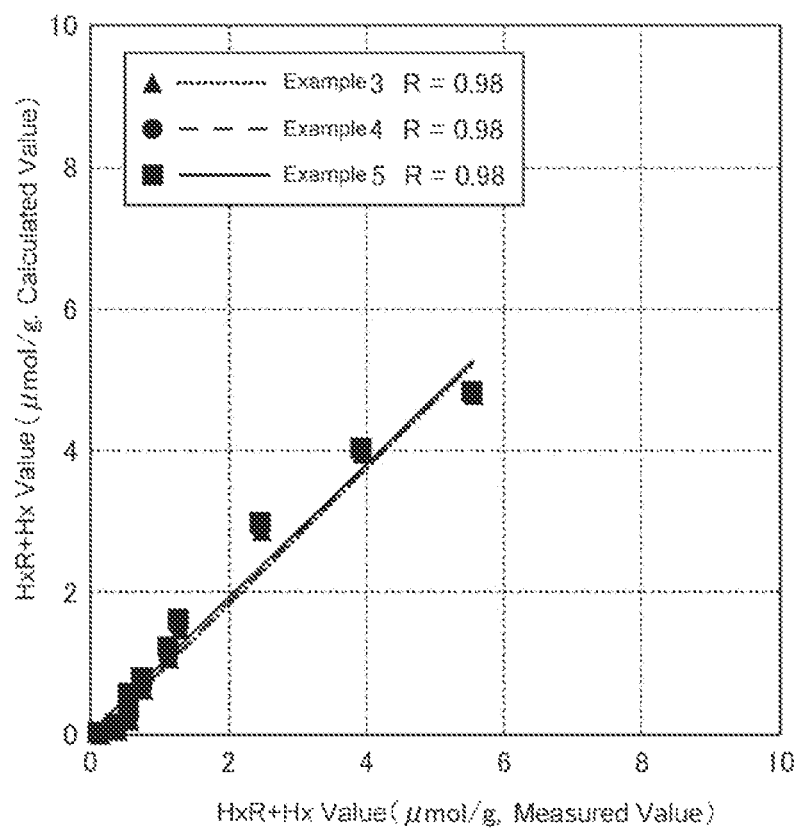
FIG. 21 is a diagram indicating a comparative example of measured and simulated HxR Hx values in sweetfish at a storage temperature of 15° C.

FIG. 19 is a diagram indicating a comparison of measured values and simulated values at the same storage times, with different numbers of rate constants in Example 3 to Example 5, for values that are the sums of the concentrations of ATP, ADP, and AMP (hereinafter referred to as the ATP+ADP+AMP values) at a storage temperature of 15° C. Additionally, FIG. 20 is a diagram indicating a comparison of measured values and simulated values at the same storage times, in Example 3 to Example 5, for IMP values. FIG. 21 is a diagram indicating a comparison of measured values and simulated values at the same storage times, in Example 3 to Example 5, for values that are the sums of the concentrations of HxR and Hx (hereinafter referred to as HxR+Hx values). For the ATP+ADP+AMP values indicated in FIG. 19, the correlation coefficients (R) between the simulated values and the measured values were approximately 0.94 in Example 3, approximately 0.95 in Example 4, and approximately 0.99 in Example 5, which are reasonable values. For the IMP values indicated in FIG. 20, the correlation coefficients (R) between the simulated values and the measured values were approximately 0.89 in Example 3, approximately 0.90 in Example 4, and approximately 0.96 in Example 5, which are reasonable values. For the HxR+Hx values indicated in FIG. 21, the correlation coefficients (R) between the simulated values and the measured values were approximately 0.98 in all of Example 3 to Example 5, which is a reasonable value. In all of the cases, there was a good fit between the measured values and the simulated values. Particularly in Example 5, there were two rate constants, thus clearly demonstrating that highly accurate simulation results can be obtained even if there are extremely few processing steps determining those values.

Figure 22:
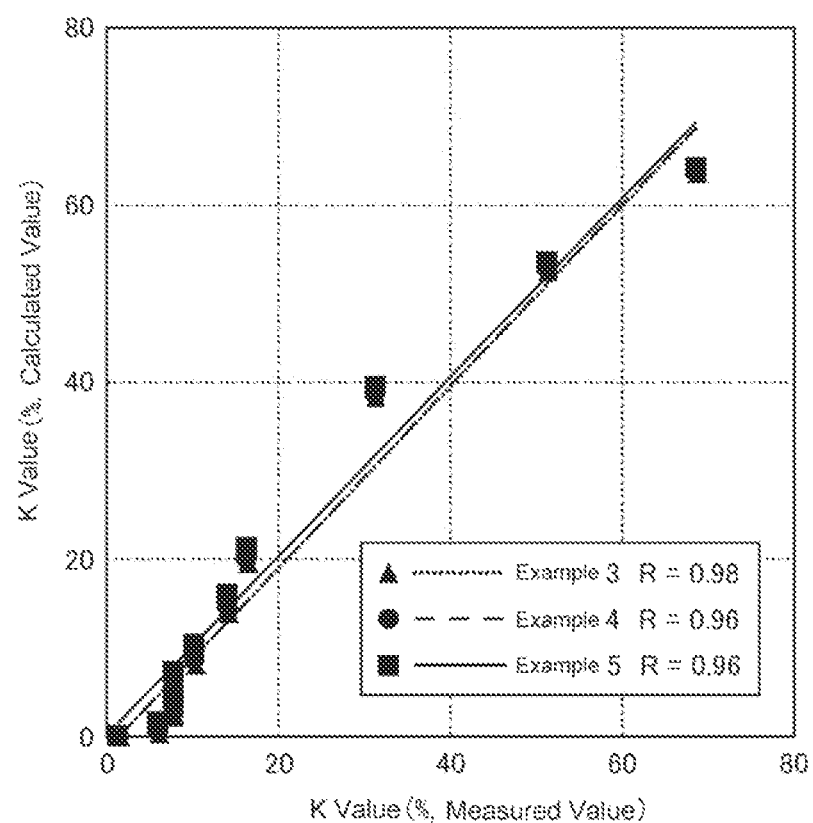
FIG. 22 is a diagram indicating a comparative example of measured and simulated K values in sweetfish at a storage temperature of 15° C.

FIG. 22 is a diagram indicating a comparison of measured and simulated K values with different numbers of rate constants in Example 3 to Example 5. The correlation coefficients (R) between the simulated values and the measured values of the K values were approximately 0.98 in Example 3, approximately 0.96 in Example 4, and approximately 0.96 in Example 5, which are reasonable values. For K values also, there was a good fit between the measured values and the simulated values. Particularly in Example 5, there were two rate constants, thus clearly demonstrating that highly accurate simulation results can be obtained even if there are extremely few processing steps determining those values.

Example 6 to Example 19

Next, using an ATP-associated compound concentration calculation computation method relating to the two-step sequential reactions ATP+ADP+AMP→IMP and IMP→HxR Hx indicated in FIG. 5 as the sequential reactions, simulations were performed with the aquatic animal species in Example 6 to Example 19 indicated in Table 1, using the storage temperatures and rate constants indicated in said table. Aside from the fact that the storage temperatures and the rate constants indicated in Table 1 and the ATP-associated compound concentration calculation computation method relating to the two-step sequential reactions were used, the same method as that in Example 5 was used to compute the ATP-associated compound concentrations and the K values at the true centers (x=0, Y=length of fish body of each fish species÷2, Z=0) of the respective fish bodies. As examples, comparisons of measured values and simulated values of the K values at the same storage times are indicated for chub mackerel (Example 6) in FIG. 23 and for Japanese jack mackerel (Example 7) in FIG. 24. Similarly determined correlation coefficients are also indicated in Table 1 regarding Example 5 to Example 19, including the aforementioned Example 5.

TABLE 1

| | Aquatic Animal Species | Correlation Coefficient (R) | Reaction Rate Constant | | Storage Temp. (° C.) |
|---|---|---|---|---|---|
| | | | k6 | k7 | |
| Example 5 | sweetfish | 0.96 | 0.5000 | 0.0109 | 15 |
| Example 6 | chub mackerel | 0.99 | 0.0972 | 0.0024 | 0 |
| Example 7 | Japanese jack mackerel | 0.99 | 0.1096 | 0.0014 | 0 |
| Example 8 | olive flounder | 0.95 | 0.0081 | 0.0080 | 0 |
| Example 9 | skipjack tuna | 0.99 | 0.0420 | 0.0041 | 0 |
| Example 10 | Pacific saury | 0.95 | 0.8000 | 0.0011 | 0 |
| Example 11 | Japanese amberjack | 0.99 | 0.4000 | 0.0065 | 0 |
| Example 12 | red seabream | 0.97 | 0.0034 | 0.0034 | 0 |
| Example 13 | young Japanese amberjack | 0.98 | 0.0986 | 0.0024 | 0 |
| Example 14 | Spanish mackerel | 0.98 | 0.1000 | 0.0010 | 0 |
| Example 15 | Japanese pilchard | 0.99 | 0.0972 | 0.0016 | 0 |
| Example 16 | Japanese flying squid | 0.99 | 0.0916 | 0.0158 | −6 |
| Example 17 | Toyama shrimp | 0.99 | 0.0169 | 0.0083 | −6 |
| Example 18 | scallop | 0.99 | 0.0161 | 0.0031 | −5 |
| Example 19 | sea urchin | 0.99 | 0.0045 | 0.0076 | 5 |

Figure 23:
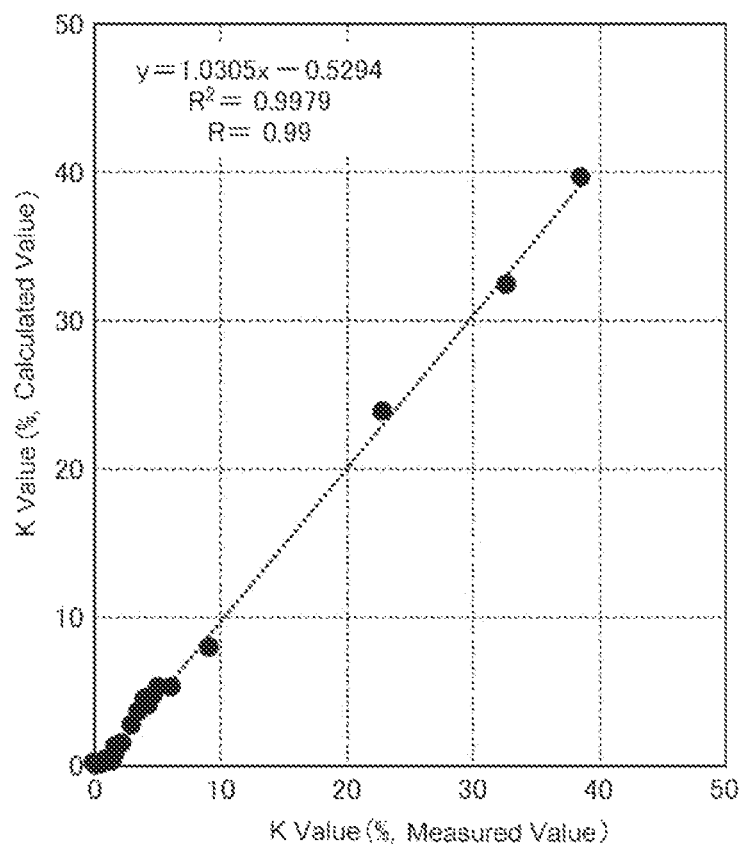
FIG. 23 is a diagram indicating a comparative example of measured and simulated K values in chub mackerel.
Figure 24:
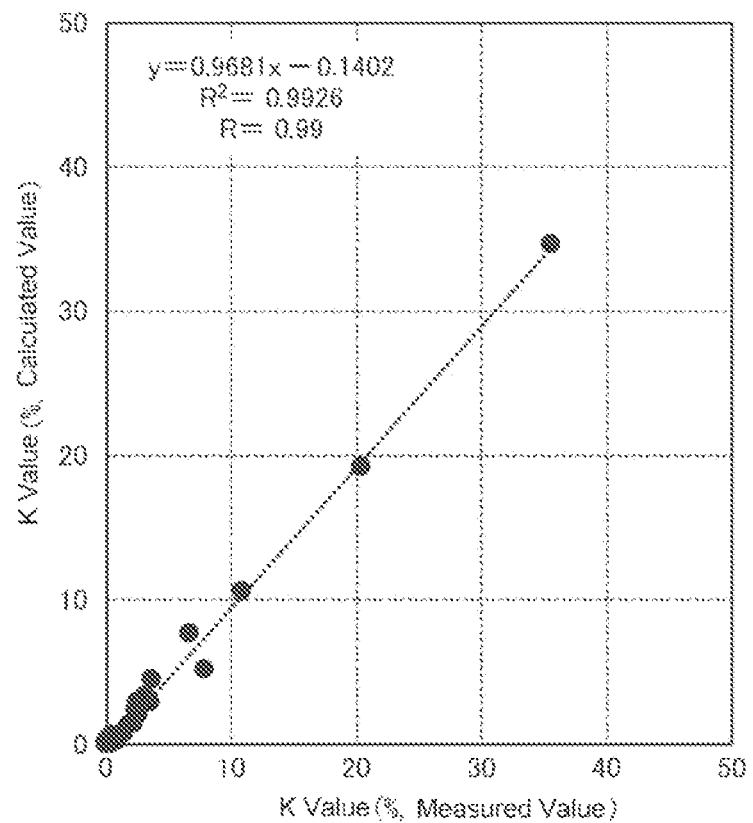
FIG. 24 is a diagram indicating a comparative example of measured and simulated K values in Japanese jack mackerel.

For the K values in Example 6 and Example 7 indicated in FIG. 23 and FIG. 24, the correlation coefficients (R) between the simulated values and the measured values were approximately 0.99 in both cases, which is a reasonable value. Additionally, in Example 8 to Example 19 indicated in Table 1 also, the correlation coefficients (R) between the simulated values and the measured values were 0.95 or higher, which are reasonable values. In all of the cases, there was a good fit between the measured values and the simulated values, thus clearly demonstrating that highly accurate results can be obtained even in simulations with two reaction rate constants, in which there are extremely few processing steps determining those values and which can thus be computed in an extremely short time. Statistically, the correlation can be determined to be sufficient if the correlation coefficient (R) is 0.7 or higher. Thus, the present simulations can be determined to have extremely good accuracy.

Example 20

Figure 25:
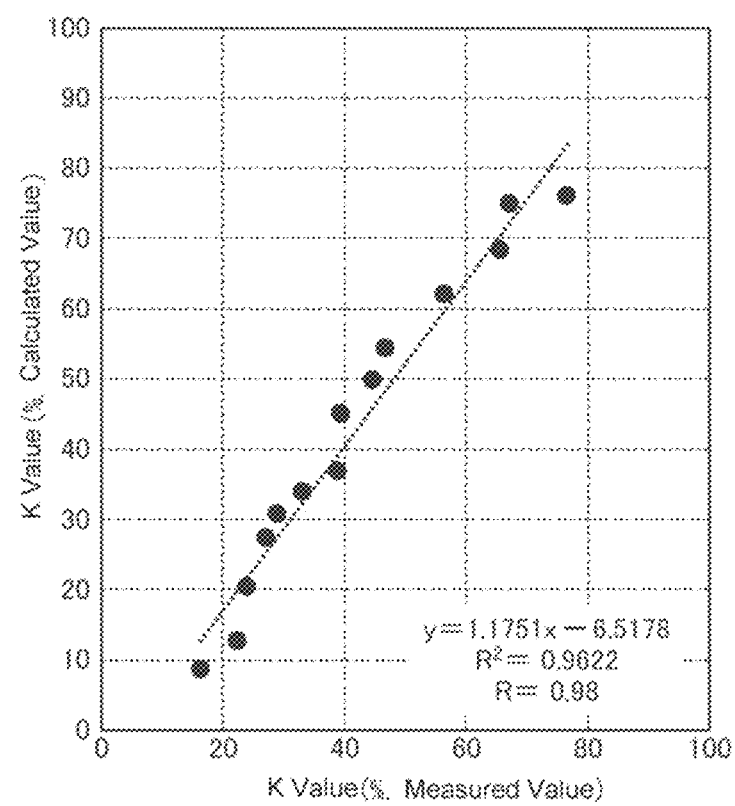
FIG. 25 is a diagram indicating a comparative example of measured and simulated K values in beef.

Next, the suitability of the present simulations for animals other than aquatic animals was studied. Specifically, using an ATP-associated compound concentration calculation computation method relating to the two-step sequential reactions ATP+ADP+AMP→IMP and IMP HxR Hx indicated in FIG. 5 as the sequential reactions, simulations were performed on beef at a storage temperature of 2° C. The ATP-associated compound concentrations and the K values were computed, using documented data (k=0.467, ρ=1053, c=3412, Q=0) (Non-Patent Document 9) as the constants data necessary for the solution to the unsteady heat conduction equation, at the center P (0, 7.5, 0) of a lump of beef having a width (X coordinate) of 15 cm, a length (Y coordinate) of 15 cm, and a height (Z coordinate) of 3 cm, with the temperatures at the surface and the center of the lump of beef being 35° C. immediately before commencing storage. The initial ATP molar concentration was 6.0 μm/g, the storage time was 750 hours, the storage temperature was 2° C., and the reaction rate constants k6=0.7000 and k7=0.0019 were used. The reaction rate constants used here were determined so as to minimize the error between the measured values (Non-Patent Document 5) and the simulated values. FIG. 25 indicates a comparison between measured values (Non-Patent Document 5) and simulated values at the same storage times for the K values in beef. For the K values in Example 20 indicated in FIG. 25, the correlation coefficient (R) between the simulated values and the measured values was approximately 0.98, which is a reasonable value.

Example 21

Figure 26:
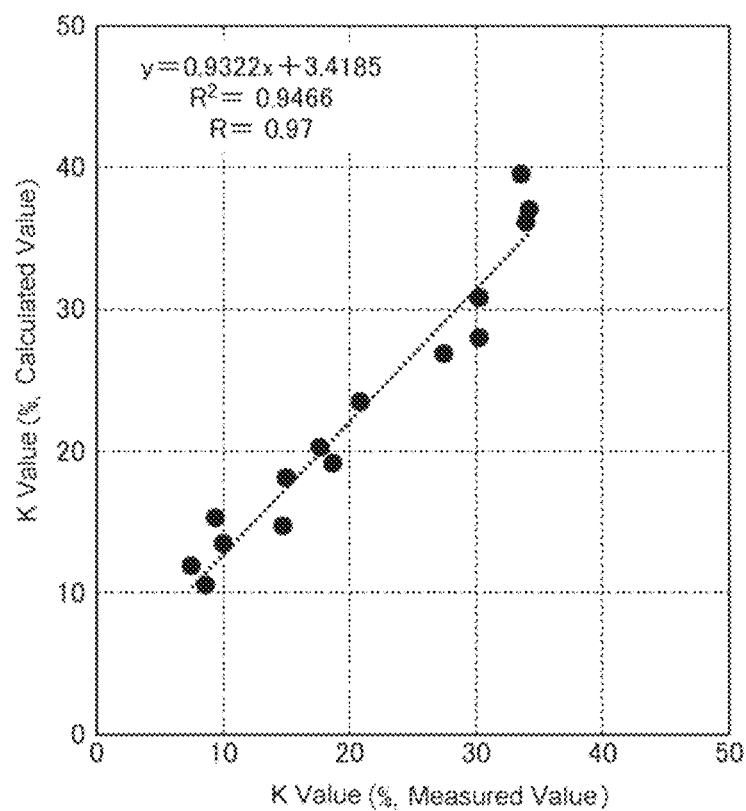
FIG. 26 is a diagram indicating a comparative example of measured and simulated K values in chicken.

Next, simulations were performed for chicken at a storage temperature of 3° C. in a manner similar to Example 20 above. The ATP-associated compound concentrations and the K values were computed, using documented data (k=0.513, ρ=1062, c=3591, Q=0) (Non-Patent Document 9) as the constants data necessary for the solution to the unsteady heat conduction equation, at the center P (0, 7.5, 0) of a lump of chicken having a width (X coordinate) of 15 cm, a length (Y coordinate) of 15 cm, and a height (Z coordinate) of 3 cm, with the temperatures at the surface and the center of the chicken being 35° C. immediately before commencing storage. The initial ATP molar concentration was 9.4 μm/g, the storage time was 300 hours, the storage temperature was 3° C., and the reaction rate constants k6=0.1990 and k7=0.0014 were used. The reaction rate constants used here were determined so as to minimize the error between the measured values (Non-Patent Document 6) and the simulated values. FIG. 26 indicates a comparison between measured values (Non-Patent Document 6) and simulated values at the same storage times for the K values in chicken. For the K values in Example 20 indicated in FIG. 26, the correlation coefficient (R) between the simulated values and the measured values was approximately 0.97, which is a reasonable value.

Example 22

Next, simulations were performed for pork at a storage temperature of 4° C. in a manner similar to Example 20 above. The ATP-associated compound concentrations and corrected K values (hereinafter referred to as mK values) were computed, using documented data (k=0.502, ρ=1130, c=3433, 0=0) (Non-Patent Document 9) as the constants data necessary for the solution to the unsteady heat conduction equation, at the centers P (0, 7.5, 0) of lumps of pork having a width (X coordinate) of 15 cm, a length (Y coordinate) of 15 cm, and a height (Z coordinate) of 3 cm, with the temperatures at the surface and at the center of each lump of pork being 35° C. immediately before commencing storage. The mK value is a freshness evaluating method (Non-Patent Document 7) that is specific to pork, determined by the expression indicated below, $$mK \text{ value } (\%) = ((HxR+Hx)/(IMP+HxR+Hx)) \times 100 \quad (26)$$

In the present example, the freshness/degree of maturation evaluation unit 14, based on the temporal change in the mK value, computes the storage time until the mK value becomes a preset value (prescribed threshold value), or computes the mK value in the food animal at a preset storage time (prescribed threshold value). Furthermore, the freshness/degree of maturation evaluation unit 15 compares the evaluation results from the freshness/degree of maturation evaluation unit 14 with a preset threshold value (prescribed threshold value) to assess the level of quality in the freshness and/or the degree of maturation in the food animal.

The initial ATP molar concentration was 10 μm/g, the storage time was 300 hours, the storage temperature was 4°

C., and the rates r6=0.5000 and r7=0.0016 were used. The reaction rate constants used here were determined so as to minimize the error between the measured values (Non-Patent Document 7) and the simulated values.

Example 23

Next, simulations were performed for boar meat at a storage temperature of 0° C. in a manner similar to Example 20 above. The ATP-associated compound concentrations and the K values were computed, using data (k=0.5020, ρ=1130, c=3433, 0=0) (Non-Patent Document 9) for pigs, which have similarly shaped bodies, as the constants data for boar meat, which was unavailable, necessary for the solution to the unsteady heat conduction equation, at the center P (0, 7.5, 0) of a lump of boar meat having a width (X coordinate) of 15 cm, a length (Y coordinate) of 15 cm, and a height (Z coordinate) of 3 cm, with the temperatures at the surface and the center of the boar meat being 35° C. immediately before commencing storage. The initial ATP molar concentration was 10.0 μm/g, the storage time was 400 hours, the storage temperature was 0° C., and the reaction rate constants k6=0.3000 and k7=0.0035 were used. The reaction rate constants used here were determined so as to minimize the error between the measured values (Non-Patent Document 8) and the simulated values. The correlation coefficients (R), the reaction rate constants, and the storage temperatures (° C.) for Example 20 to Example 23 are indicated together in Table 2.

TABLE 2

| Livestock Animal Species | Correlation Coefficient (R) | Reaction Rate Constant | | Storage Temp. (° C.) |
| --- | --- | --- | --- | --- |
| | | k6 | k7 | |
| Example 20 cow | 0.98 | 0.7000 | 0.0019 | 2 |
| Example 21 chicken | 0.99 | 0.1990 | 0.0014 | 3 |
| Example 22 pig | 0.97 | 0.5000 | 0.0016 | 4 |
| Example 23 boar | 0.97 | 0.3000 | 0.0035 | 0 |

In Example 20 to Example 23 indicated in Table 2, the correlation coefficients (R) between the simulated values and the measured values were 0.97 or higher, which are reasonable values. In all of the cases, there was a good fit between the measured values and the simulated values, thus clearly demonstrating that highly accurate results can be obtained even in simulations with two reaction rate constants, in which there are extremely few processing steps determining those values and which can thus be computed in an extremely short time. Additionally, from the results in Table 2, it is clear that freshness/degree of maturation evaluations in livestock animals are possible by the present simulation method.

Example 24

Figure 27:
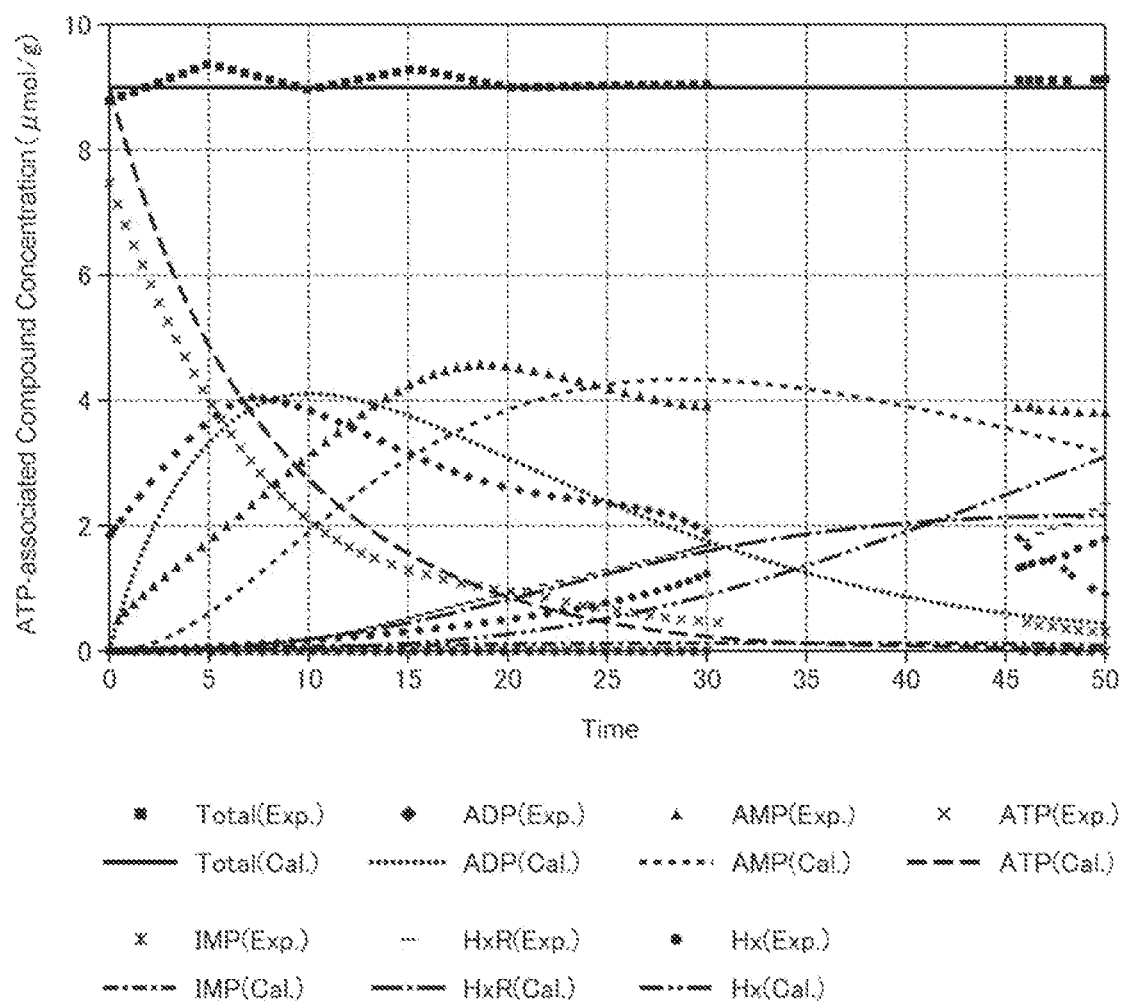
FIG. 27 is a diagram indicating a comparative example of measured and simulated ATP-associated compound concentrations in Japanese flying squid.
Figure 28:
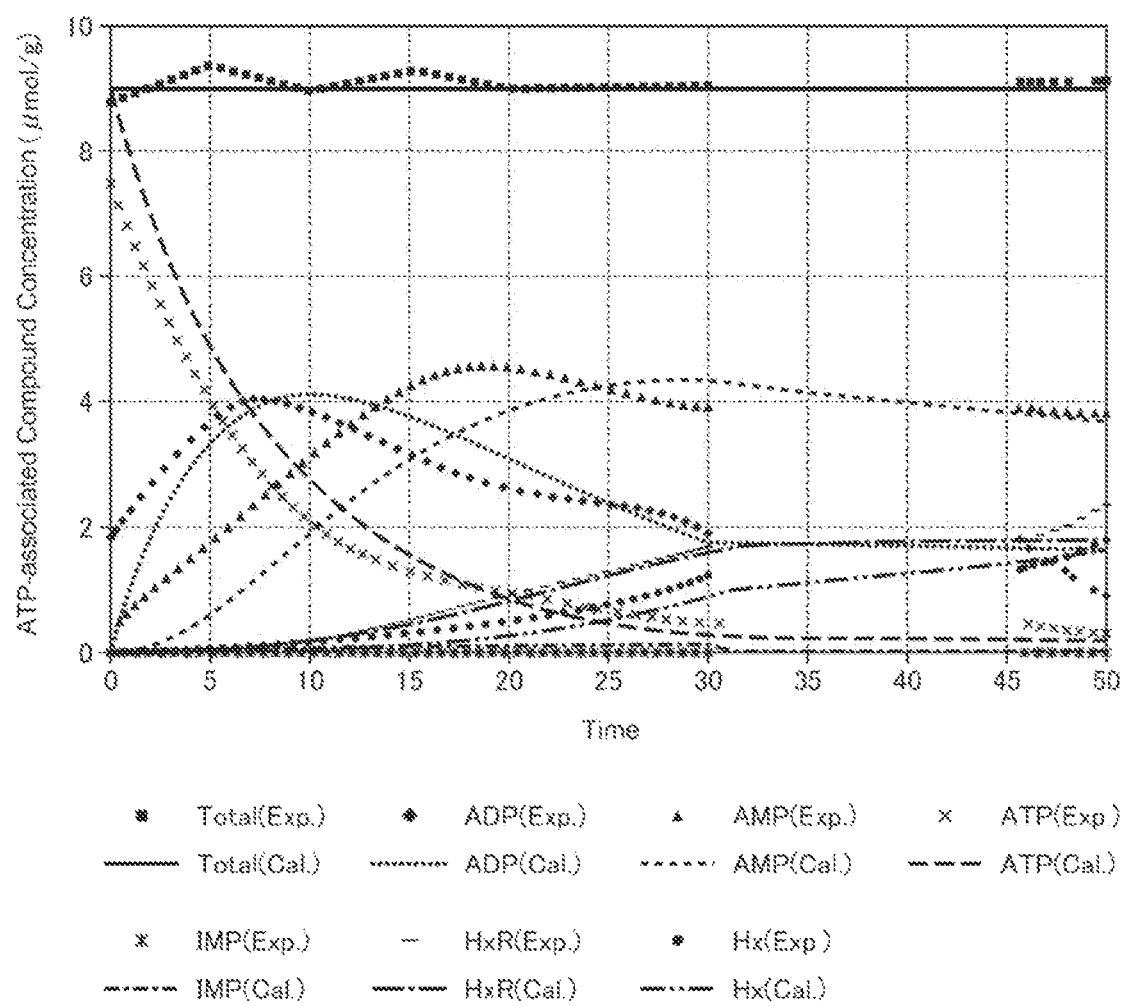
FIG. 28 is a diagram indicating a comparative example of measured and simulated ATP-associated compound concentrations in Japanese flying squid.

The invention was implemented for cases in which the various reaction rates were changed in accordance with the storage times for Japanese flying squid at a storage temperature of −6° C. The fish body center P (0, 12.5, 0) was computed, using the average values for thirteen common fish species (k=0.4277, ρ=999.8, c=3564.2, =0) as the constants data necessary for the solution to the unsteady heat conduction equation, for a Japanese flying squid having a width (X coordinate) of 7 cm, a length (Y coordinate) of 25 cm, and a height (Z coordinate) of 7 cm, with the temperatures at the surface and the center of the Japanese flying squid initially being 20° C. immediately before commencing storage, the initial ATP molar concentration being 10 μm/g, the storage time being 50 hours, and the storage temperature being 6° C. Next, a simulation of the ATP-associated compound concentrations was performed for an ATP-associated compound concentration calculation computation method relating to the five-step sequential reactions ATP→ADP, ADP AMP, AMP→IMP, IMP→HxR, and HxR→Hx indicated in FIG. 4. FIG. 27 is a diagram indicating ATP-associated compound concentration changes using conventional methods (r1=0.1100, r2=0.0800, r3=0.0300, r4=1.1600, and r5=0.0500) for 50 hours after commencing storage. Meanwhile, FIG. 28 is a diagram for the case in which ATP-associated compound concentration changes are computed by using the aforementioned reaction rates up to 30 hours after commencing storage, then computing the ATP-associated compound concentrations by changing the reaction rates to r1=0.0100, r2=0.0100, r3=0.0100, r4=1.0000, and r5=0.0200 after 30 hours. FIG. 27 shows that the simulated values and the measured values are relatively well-matched up to 30 hours at the storage temperature, yet that a difference arises in the values at and later than 45 hours. Meanwhile, the values are well-matched even at and later than 45 hours in FIG. 28. Thus, it was observed that more accurate results can be obtained by obtaining simulation results by changing the reaction rates as needed.

Example 25

Figure 29:
FIG. 29 is a diagram illustrating an example of a display of calculation results.
Figure 30:
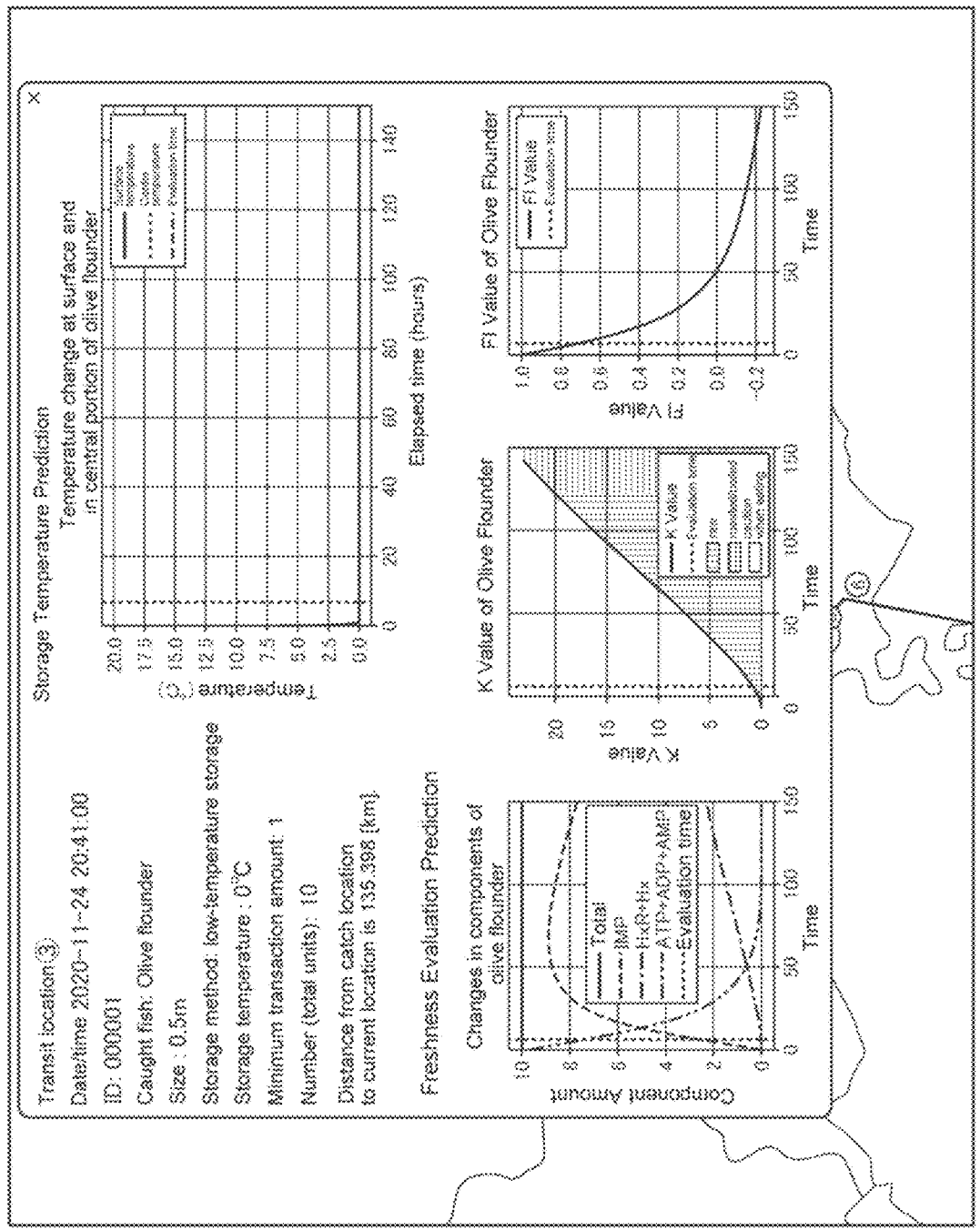
FIG. 30 is a diagram illustrating an example of a display of calculation results.

Next, examples of displays of the calculation results for olive flounder when using an ATP-associated compound concentration calculation computation method relating to the two-step sequential reactions ATP+ADP+AMP→IMP and IMP→HxR+Hx indicated in FIG. 5 as the sequential reactions are illustrated in FIG. 29 and FIG. 30. As illustrated in FIG. 29, the system involves sequentially displaying the transportation path on a map. Additionally, as illustrated in FIG. 30, by designating a transit location on the map, the temperature change and the freshness (K value and FI value) at that time are displayed on the map, and in addition thereto, the evaluation time is displayed on a graph, thereby providing the function of allowing the freshness and the storage temperature at the evaluation time to be visually confirmed. Furthermore, the invention has the function wherein, in the case in which there has been an outbreak of an infectious disease among distribution-associated people on the distribution path, if it is determined that a food animal is unsafe to eat or if it is determined that considerable caution is necessary from freshness/degree of maturation assessment results and processing information based on fishing/processing person data, distribution transit location information, and disinfection/sterilization data, then the outbreak points and sterilization/disinfection processing points, as well as information relating thereto, cautionary information, and the like can be displayed on the map, and visually confirmed.

Example 26

Figure 31:
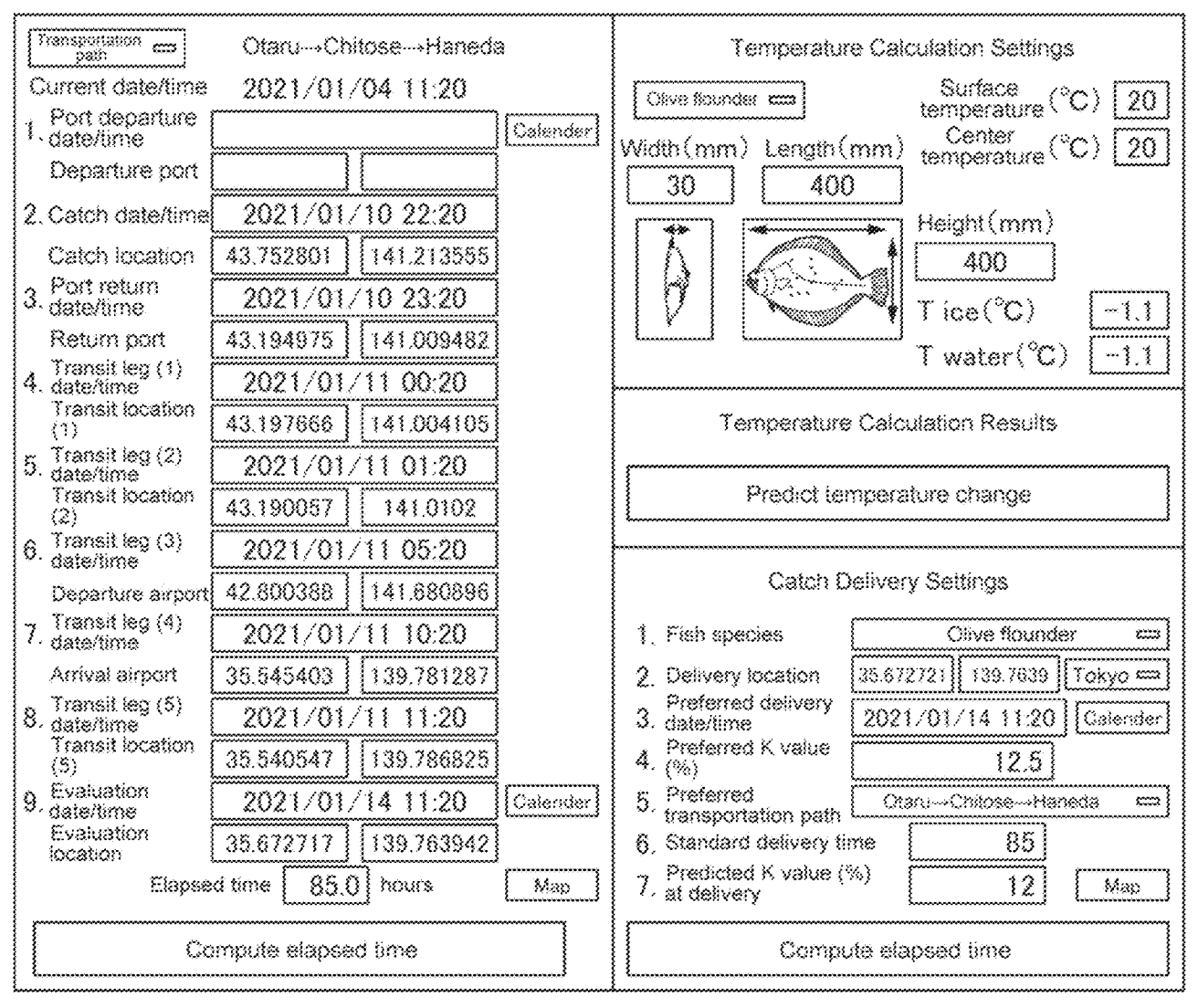

Next, an example of a function using an ATP-associated compound concentration calculation computation method relating to the two-step sequential reactions ATP+ADP+ AMP IMP and IMP→HxR Hx indicated in FIG. 5, as the sequential reactions, to compute necessary conditions, such as preservation temperature and preservation time, that have been optimized from information in a freshness evaluation system for olive flounder, and automatically input as transportation conditions at the time of placing an order, will be indicated. For example, when wishing to obtain a food animal with a designated K value, the time and the month and day on which the food animal should be caught and commence being transported is determined by computing backwards from the simulation results by the present freshness evaluation system (FIG. 31). In this case, the K value and the transportation time at the time of delivery are also displayed. Additionally, this information may be displayed on a map, as illustrated in FIG. 29 and FIG. 30. By finalizing an order after confirming the freshness information, the path information, and the predicted arrival times at the respective locations, fishery-associated people can be notified of catch information so that a designated fish species can be prepared and sent on the required day and time.

Modified Examples

The present invention is not limited to the embodiments described above, and various modifications are possible within the scope indicated in the claims. Embodiments obtained by appropriately combining the technical means disclosed respectively for the different embodiments are also included within the technical scope of the present invention.

For example, the parameter calculation unit 8 and the evaluation calculation execution unit 9 may be provided as computation devices and may be realized as devices that are independent of the other functional blocks. Similarly, the freshness/degree of maturation evaluation unit 14 and the freshness/degree of maturation assessment unit 15 may be realized as independent devices in the form of freshness/degree of maturation evaluating devices.

Furthermore, the computation device 5, the parameter calculation unit 8, the data storage device 4, and the evaluation calculation execution unit 9 described above may be constituted by hardware logic, or may be realized by software using a CPU as indicated below.

That is, they can be achieved by preparing a recording medium having, recorded in a computer-readable manner, program code (an executable-type program, an intermediate code program, or a source program) for control programs (temperature parameter calculation program, rate constant parameter calculation program, data regarding rate constants) for the parameter calculation unit 8 and the evaluation calculation execution unit 9, which is software for realizing the above-mentioned functions, and by having the program code recorded in the above-mentioned recording medium be read out and executed by a computer (or a CPU or an MPU (micro-processing unit)) provided with a CPU (central processing unit) for executing commands of the control programs for realizing the respective functions, a ROM (read-only memory) in which the above-mentioned programs are stored, a RAM (random access memory) in which the above-mentioned programs are loaded, a storage device (recording medium) such as a memory storing the aforementioned programs and various types of data, etc.

As the above-mentioned recording medium, it is possible to use, for example, tape-type media such as magnetic tapes and cassette tapes, disk-type media including magnetic disks such as floppy (registered trademark) disks and hard disks, and optical disks such as CD-ROM/MO/MD/DVD/CD-R, card-type media such as IC cards (including memory cards) and optical cards, or semiconductor memory-type media such as mask ROM/EPROM/EEPROM/flash ROM, etc.

Additionally, the input device 2, the data storage device 4, the data input unit 7, the parameter calculation unit 8 and the evaluation calculation execution unit 9, the data output unit 10, and the output device 3 may be configured to be capable of connecting to a communication network, and input data, output data, and the above-mentioned program code may be supplied via the communication network. This communication network is not particularly limited, and it is possible to use, for example, the internet, an intranet, an extranet, a LAN, an ISDN, a VAN, a CATV communication network, a VPN (virtual private network), a telephone line network, a mobile communication network, a satellite communication network, etc. Additionally, the transmission medium constituting the communication network is not particularly limited, and it is possible to use, for example, physical lines such as IEEE 1394, USB, USB 2.0, USB 3.0, USB Type-c, USB 3.1 Gen 1, USB 3.1 Gen 2, Thunderbolt 3, microUSB, USB PD, Lightning, power line carriers, cable TV lines, telephone lines, and ADSL lines, or wireless connections such as infrared rays like those for IrDA or remote controls, Bluetooth (registered trademark), IEEE 802.11, IEEE 802.11a, IEEE 802.11b, IEEE 802.11g, IEEE 802.11j, IEEE 802.11n (Wi-Fi 4), IEEE 802.11i, IEEE 802.11ac (Wi-Fi 5), IEEE 802.11ad, IEEE 802.11af, IEEE 802.11 ax (Wi-Fi 6), IEEE 802.11ah, IEEE 802.11p, HDR, cellular telephone networks, satellite links, and terrestrial digital networks. The present invention may be realized in the form of computer data signals embedded in carrier waves in which the above-mentioned program code is realized by electronic transmission.

Furthermore, the freshness/degree of maturation evaluating device or a program that performs the freshness/degree of maturation evaluating method mentioned above may be realized by being installed in a fishing vessel, a fish box, a refrigerator, a refrigerator/freezer, etc.

INDUSTRIAL APPLICABILITY

The product and method of the present invention can be used, at a market or at a distribution site for food animals, by a producer, a market-associated person, a distribution-associated person, or a consumer, requiring assessments of the level of quality or the like regarding freshness/degree of maturation, as well as quality control, distribution control, storage temperature control, etc. of the food animals.

REFERENCE SIGNS LIST

1 Freshness/degree of maturation evaluating device
2 Input device
3 Output device
4 Data storage device
5 Computation device
6 Work memory
7 Data input unit
8 Parameter calculation unit
9 Evaluation calculation execution unit
10 Data output unit
11 Temperature parameter calculation unit
12 Rate constant parameter calculation unit
13 ATP-associated compound concentration calculation unit
14 Freshness/degree of maturation evaluation unit
15 Freshness/degree of maturation assessment unit
S1 Temperature parameter calculation
S2 Rate constant parameter calculation
S3 ATP-associated compound concentration calculation
S4 Freshness/degree of maturation evaluation
S5 Freshness/degree of maturation assessment

The invention claimed is:

1. A freshness/degree of maturation evaluating device for evaluating a freshness and/or a degree of maturation of a food animal, the freshness/degree of maturation evaluating device comprising:
a temperature parameter calculation unit that calculates a temperature parameter regarding a storage time and a temperature in an arbitrary area inside the food animal, the parameter being based on the temperature in the arbitrary area inside the food animal, determined by the storage time and an unsteady heat conduction equation;
a rate constant parameter calculation unit that calculates a rate constant parameter regarding sequential decomposition reactions of various adenosine triphosphate (ATP)-associated compounds contained in the food animal, the parameter being set based on rate constants in the food animal determined by using a relation based on the storage time of the food animal and measured values of ATP-associated compound concentrations;
an ATP-associated compound concentration calculation unit that calculates the ATP-associated compound concentrations by a sequential decomposition reaction calculation model using the temperature parameter and the rate constant parameter;
a freshness/degree of maturation evaluation unit that computes a freshness indicator K value and/or an FI value from the ATP-associated compound concentrations, and
a freshness/degree of maturation assessment unit that computes an optimized storage temperature for the food animal based on the K value and/or FI value, and automatically inputs the optimized storage temperature as a first initial settings value for transportation conditions.

2. The freshness/degree of maturation evaluating device according to claim 1, wherein the food animal is an aquatic animal.

3. The freshness/degree of maturation evaluating device according to claim 2, wherein the aquatic animal is one of sweetfish, chub mackerel, Japanese jack mackerel, olive flounder, skipjack tuna, Pacific saury, Japanese amberjack, red seabream, young Japanese amberjack, Spanish mackerel, Japanese pilchard, Japanese flying squid, Toyama shrimp, scallop, and sea urchin.

4. The freshness/degree of maturation evaluating device according to claim 1, wherein the food animal is a livestock animal.

5. The freshness/degree of maturation evaluating device according to claim 4, wherein the livestock animal is one of a cow, a chicken, a pig, and a boar.

6. The freshness/degree of maturation evaluating device according to claim 1, wherein at least two and at most ten of the rate constant parameters are used.

7. The freshness/degree of maturation evaluating device according to claim 1, wherein the freshness/degree of maturation evaluation unit further evaluates the freshness and/or the degree of maturation of the food animal by comparing at least one of the K value, the FI value, or an inosinic acid (IMP) value with a prescribed threshold value.

8. The freshness/degree of maturation evaluating device according to claim 7, wherein the freshness/degree of maturation assessment unit that assesses the freshness and/or the degree of maturation by comparing an evaluation result by the freshness/degree of maturation evaluation unit with a prescribed threshold value.

9. The freshness/degree of maturation evaluating device according to claim 8, wherein the freshness/degree of maturation assessment unit has functions for assessing the freshness and/or the degree of maturation of the food animal by comparing at least one of the K value, the FI value, or the IMP value with a prescribed threshold value, and for displaying optimal recommended cooking information regarding an ingredient in accordance with the assessment result.

10. The freshness/degree of maturation evaluating device according to claim 8, wherein the freshness/degree of maturation assessment unit has a system for sequentially displaying, on a map, arbitrary waypoints on a transportation path, and has a function wherein, when a transit location is designated on the map, a temperature change and freshness information at a relevant location on the map, and a freshness or a storage temperature at a designated time can be visually confirmed.

11. The freshness/degree of maturation evaluating device according to claim 8, wherein the freshness/degree of maturation assessment unit has functions for computing necessary conditions, including at least one of a storage time, a transportation method, a transportation path, a catch/slaughter date/time, and a transportation commencement date/time, satisfying ordering conditions, and for automatically inputting initial settings values, including the first initial settings value, for transportation conditions satisfying consumer needs.

12. The freshness/degree of maturation evaluating device according to claim 8, wherein the freshness/degree of maturation assessment unit has functions for displaying cautionary information, in a case in which there has been an outbreak of an infectious disease among distribution-associated people on a distribution path, and if a food animal is determined to be unsafe to eat or if considerable caution is determined to be necessary from the freshness/degree of maturation assessment results and processing information based on fishery-, slaughter-, processing-, market-, and distribution-associated person data, distribution transit location information, and disinfection/sterilization data.

13. The freshness/degree of maturation evaluating device according to claim 1, wherein the freshness/degree of maturation evaluation unit computes a corrected (mK) value from the ATP-associated compound concentrations, and further evaluates the freshness and/or the degree of maturation of the food animal by comparing the corrected (mK) value or both the corrected (mK) value and an IMP value with a prescribed threshold value.

14. The freshness/degree of maturation evaluating device according to claim 13, wherein the freshness/degree of maturation assessment unit assesses the freshness and/or the degree of maturation by comparing an evaluation result by the freshness/degree of maturation evaluation unit with a prescribed threshold value.

15. The freshness/degree of maturation evaluating device according to claim 14, wherein the freshness/degree of maturation assessment unit has functions for assessing the freshness and/or the degree of maturation of the food animal by comparing the mK value or both the mK value and the IMP value with a prescribed threshold value, and for displaying optimal recommended cooking information regarding an ingredient in accordance with the assessment result.

16. A refrigerator/freezer provided with the freshness/degree of maturation evaluating device according to claim 1.

17. A freshness/degree of maturation evaluating device for evaluating a freshness and/or a degree of maturation of a food animal, the freshness/degree of maturation evaluating device comprising:
a rate constant parameter calculation unit that calculates a rate constant parameter regarding sequential decomposition reactions of various adenosine triphosphate (ATP)-associated compounds contained in the food animal, the parameter being set based on rate constants in the food animal determined by using a relation based on a storage time of the food animal and measured values of ATP-associated compound concentrations;

an ATP-associated compound concentration calculation unit that calculates the ATP-associated compound concentrations by a sequential decomposition reaction calculation model using a storage temperature of the food animal and the rate constant parameter;

a freshness/degree of maturation evaluation unit that computes a freshness indicator K value and/or an FI value from the ATP-associated compound concentrations, and a freshness/degree of maturation assessment unit that computes an optimized storage temperature for the food animal based on the K value and/or FI value, and automatically inputs the optimized storage temperature as a first initial settings value for transportation conditions.

18. The freshness/degree of maturation evaluating device according to claim 17, wherein the food animal is an aquatic animal.

19. The freshness/degree of maturation evaluating device according to claim 17, wherein the food animal is a livestock animal.

* * * * *